United States Patent
Chaiken et al.

(12)

(10) Patent No.: US 6,289,230 B1
(45) Date of Patent: Sep. 11, 2001

(54) TISSUE MODULATION PROCESS FOR QUANTITATIVE NONINVASIVE IN VIVO SPECTROSCOPIC ANALYSIS OF TISSUES

(75) Inventors: Joseph Chaiken, Fayetteville, NY (US); Charles M. Peterson, Potomac, MD (US)

(73) Assignee: LighTouch Medical, Inc., New Hope, PA (US)

( * ) Notice: Subject to any disclaimer, the term of this patent is extended or adjusted under 35 U.S.C. 154(b) by 0 days.

(21) Appl. No.: 09/349,061

(22) Filed: Jul. 7, 1999

Related U.S. Application Data

(60) Provisional application No. 60/091,899, filed on Jul. 7, 1998.

(51) Int. Cl.$^7$ .................................................... A61B 5/00
(52) U.S. Cl. ........................................... 600/322; 600/316
(58) Field of Search ................................... 600/310, 317, 600/322, 323, 326, 330, 335, 336, 476, 316

(56) References Cited

U.S. PATENT DOCUMENTS

| | | |
|---|---|---|
| 3,906,241 | 9/1975 | Thompson . |
| 4,169,676 | 10/1979 | Kaiser . |

(List continued on next page.)

FOREIGN PATENT DOCUMENTS

| | | |
|---|---|---|
| 1 909 882 | 9/1970 | (DE) . |
| 195 18 511 A1 | 11/1995 | (DE) . |
| 195 38 372 | 4/1997 | (DE) . |
| 0 623 308 A1 | 11/1994 | (EP) . |
| 0 637 742 | 2/1995 | (EP) . |
| 0 776 628 | 6/1997 | (EP) . |
| WO 88/06726 | 9/1988 | (WO) . |
| WO 92/15008 | 9/1992 | (WO) . |
| WO 93/00856 | 1/1993 | (WO) . |
| WO 93/12712 | 7/1993 | (WO) . |
| WO 94/10901 | 5/1994 | (WO) . |
| WO 96/39926 | 12/1996 | (WO) . |
| WO 97/13448 | 4/1997 | (WO) . |
| WO 97/20495 | 6/1997 | (WO) . |
| WO 97/36540 | 10/1997 | (WO) . |
| WO 98/03847 | 1/1998 | (WO) . |

OTHER PUBLICATIONS

Andeson, R. Rox et al., "The Optics of Human Skin," The Journal of Investigative Dermatology, Vol. 77, No. 13, 1981, pp. 13–19.

(List continued on next page.)

*Primary Examiner*—Eric F. Winakur
(74) *Attorney, Agent, or Firm*—Gates & Cooper LLP

(57) ABSTRACT

Methods are provided for noninvasively measuring blood volume and analyte concentration and for obtaining spectroscopic information relating to immobile tissues, such as skin. One method is for determining concentration of an analyte, such as glucose, in blood of a subject. The method comprises irradiating a region of tissue, such as a fingertip, of the subject with a light source; collecting fluorescence spectra emitted by the region of tissue, the quantity of fluorescence spectra being indicative of blood volume; and collecting Raman spectra emitted by the region of tissue at a wavelength range that corresponds to the analyte. The method further comprises dividing the collected Raman spectra by the collected fluorescence spectra to obtain a number proportional to the concentration of analyte per unit blood volume. The method can further comprise determining the integral of net collected spectra, net collected spectra being a difference between spectra collected while the region of tissue is in a blood-replete state and spectra collected while the region of tissue is in a blood-depleted state. The method can further comprise enhancing the spectra collected by performing adjacent averaging smoothing operations. Blood volume in a region of tissue for spectroscopic measurement can be modulated by applying an ultrasonic transducer to the region of tissue, and also be applying a tourniquet.

32 Claims, 11 Drawing Sheets

U.S. PATENT DOCUMENTS

| | | |
|---|---|---|
| 4,427,889 | 1/1984 | Müller . |
| 4,655,225 | 4/1987 | Dähne et al. . |
| 4,890,619 * | 1/1990 | Hatschek ............................. 600/323 |
| 4,975,581 | 12/1990 | Robinson et al. . |
| 5,086,229 | 2/1992 | Rosenthal et al. . |
| 5,159,929 | 11/1992 | Morris et al. . |
| 5,194,913 | 3/1993 | Myrick et al. . |
| 5,243,983 | 9/1993 | Tarr et al. . |
| 5,261,410 | 11/1993 | Alfano et al. . |
| 5,370,114 | 12/1994 | Wong et al. . |
| 5,372,135 | 12/1994 | Mendelson et al. . |
| 5,510,894 | 4/1996 | Batchelder et al. . |
| 5,551,422 | 9/1996 | Simonsen et al. . |
| 5,553,616 | 9/1996 | Ham et al. . |
| 5,553,617 | 9/1996 | Barkenhagen . |
| 5,582,168 | 12/1996 | Samuels et al. . |
| 5,601,079 | 2/1997 | Wong et al. . |
| 5,615,673 | 4/1997 | Berger et al. . |
| 5,827,181 * | 10/1998 | Dias et al. ............................. 600/323 |
| 5,836,317 | 11/1998 | Kunst . |

OTHER PUBLICATIONS

Berger, Andrew J. et al., "Rapid, Noninvasive Concentration Measurement of Aqueous Biological Analytes by Near–Infrared Raman Spectroscopy," Applied Optics, Jan. 1, 1996, vol. 35, No. 1, pp. 209–212.

Berger, Andrew J. et al., "Multicomponent Blood Analysis by Near–Infrared Raman Spectroscopy," Applied Optics, vol. 38, No. 13, May 1, 1999, pp. 2916–2926.

Bhandare, Prashant et al., "Multivariate Determination of Glucose in Whole Blood Using Partial Least–Squares and Artificial Neural Networks Based on Mid–Infrared Spectroscopy," Applied Spectroscopy, Applied Spectroscopy, 1993, vol. 47, No. 8, pp. 1214–1221.

Duo, Xiaoming et al., "Biological Applications of Anti–Stokes Raman Spectroscopy: Quantitative Analysis of Glucose in Plasma and Serum by a Highly Sensitive Multichannel Raman Spectrometer," Applies Spectroscopy, 1996, vol. 50, No. 10, pp. 1301–1306.

Khalil, Omar S., "Spectroscopic and Clinical Aspects of Noninvasive Glucose Measurements," Clinical Chemistry, vol. 45, No. 2, 1999, pp. 165–177.

Robinson, M. Ries et al., "Noninvasive Glucose Monitoring in Diabetic Patients: A Preliminary Evaluation," Clin. Chem., 1992, vol. 38, No. 9, pp. 1618–1622.

Wang, Steve Y. et al., "Analysis of Metabolites in Aqueous Solutions by Using Laser Raman Spectroscopy," Applied Optics, Feb. 20, 1993, vol. 32, No. 6, pp. 925–929.

* cited by examiner

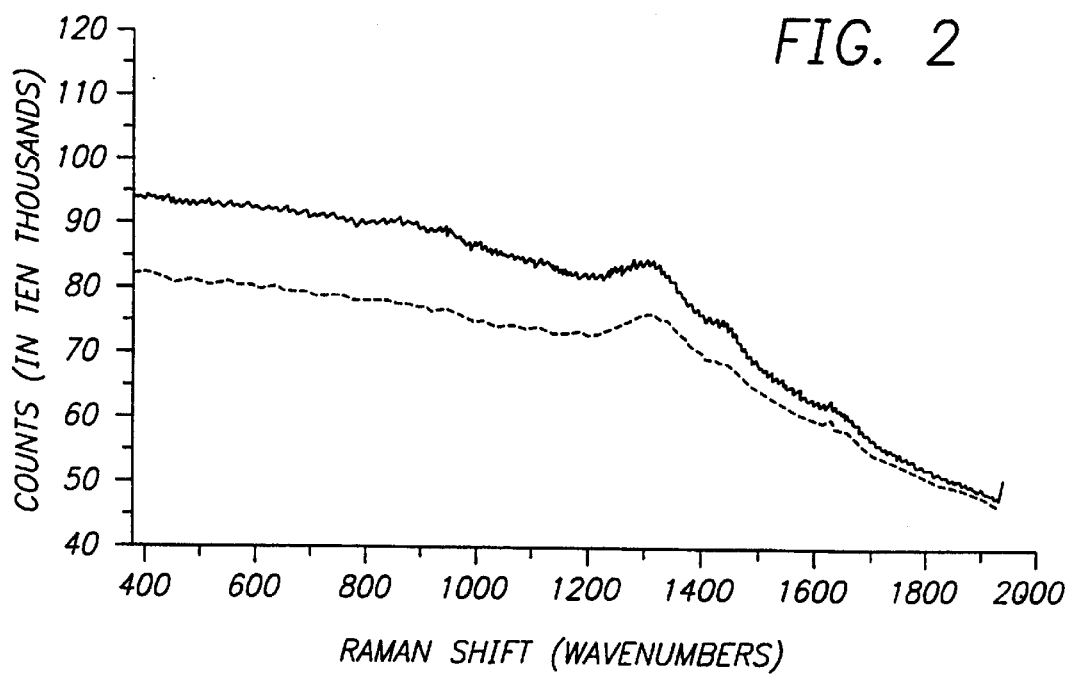
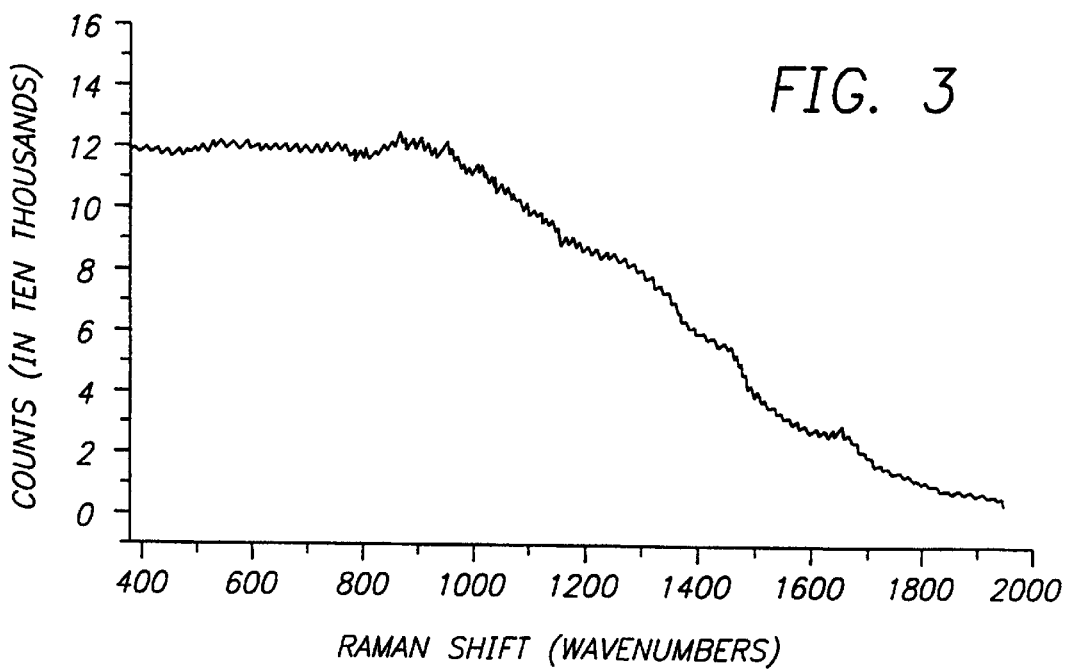

TISSUE MODULATION PROCESS FOR QUANTITATIVE NONINVASIVE IN VIVO SPECTROSCOPIC ANALYSIS OF TISSUES

This application claims the benefit of U.S. provisional patent application No. 60/091,899, filed Jul. 7, 1998, the entire contents of which are incorporated herein by reference. This application is related to U.S. patent applications Ser. Nos. 09/191,478, filed Nov. 12, 1998; 09/238,487, filed Jan. 27, 1999; and 09/295,975, filed Apr.21, 1999, the entire contents of each of which are incorporated herein by reference. Throughout this application, various publications are referenced. These publications are incorporated herein by reference in order to more fully describe the state of the art to which the invention pertains.

TECHNICAL FIELD OF THE INVENTION

The invention relates to methods for noninvasive spectroscopic examination of blood and/or other tissues. More particularly, the invention relates to methods for obtaining Raman spectroscopic features associated with both mobile and immobile tissues, including a method for determining blood volume and analyte concentration, and a method for detecting Raman spectroscopic features associated with skin.

BACKGROUND

There has long been considerable interest in the noninvasive monitoring of body chemistry. There are 16 million Americans with diabetes, all of whom would benefit from a method for non-invasive measurement of blood glucose levels. Using currently accepted methods for measuring blood glucose levels, many diabetics must give blood five to seven times per day to adequately monitor their health status. With a non-invasive blood glucose measurement, closer control could be imposed and the continuing damage, impairment and costs caused by diabetes could be minimized.

Blood oximetry is an example of an application of electronic absorption spectroscopy to non-invasive monitoring of the equilibrium between oxygenated and deoxygenated blood (U.S. Pat. No. 5,615,673, issued Apr. 1, 1997). Similarly, vibrational spectroscopy is a reliable mode of quantitative and qualitative ex vivo analysis for complex mixtures, and there are reports of in vitro applications of this method to metabolically interesting analytes (A. J. Berger et al., 1999, Multicomponent blood analysis by near infrared spectroscopy, Applied Optics 38(13):2916–2926 ; S. Y. Wang et al, 1993, Analysis of metabolites in aqueous solution by using laser Raman spectroscopy, Applied Optics 32(6):925–929; A. J. Berger et al., 1996, Rapid, noninvasive concentration measurements of aqueous biological analytes by near-infrared Raman spectroscopy, Applied Optics 35(1):209–212). Infrared measures, such as vibrational absorption spectroscopy, have been applied to skin tissue, but with success limited by unavailability of suitable light sources and detectors at crucial wavelengths, and by heating of the tissue due to the absorption of incident radiation (U.S. Pat. No. 5,551,422, see also R. R. Anderson and J. A. Parrish, 1981, The Optics of Human Skin, J. Investigative Dermatology 77(1):13–19). Previous attempts to provide methods for noninvasive blood glucose monitoring are summarized in U.S. Pat. No. 5,553,616, issued on Sep. 10, 1996, and in O. S. Khalil, 1999, Spectroscopic and clinical aspects of noninvasive glucose measurement, Clinical Chemistry 45:165–177.

Application of noninvasive techniques for blood analysis will require improved methods for isolating signals attributable to blood versus surrounding tissues.

SUMMARY OF THE INVENTION

The invention provides methods for noninvasively measuring blood volume and analyte concentration and for obtaining spectroscopic information relating to immobile tissues, such as skin. In one embodiment, the invention provides a noninvasive method of determining concentration of an analyte in blood of a subject. Examples of an analyte include, but are not limited to, glucose, urea, total protein, free fatty acids, monoglycerides, diglycerides, triglycerides, creatinine, exchangeable protein associated amide protons or cholesterol. Preferably, the analyte is glucose. The method comprises irradiating a region of tissue, such as a fingertip, of the subject with a light source; collecting fluorescence spectra emitted by the region of tissue, the quantity of fluorescence spectra being indicative of blood volume; and collecting Raman spectra emitted by the region of tissue at a wavelength range that corresponds to the analyte, the quantity of Raman spectra being indicative of the amount of analyte. The method further comprises dividing the collected Raman spectra by the collected fluorescence spectra to obtain a number that is proportional to the concentration of analyte per unit blood volume.

In a preferred embodiment, the fluorescence and Raman spectra are collected while the region of tissue is in a blood-replete state and collected while the region of tissue is in a blood-depleted state. The method further comprises determining the integral of net collected spectra, net collected spectra being a difference between spectra collected while the region of tissue is in a blood-replete state and spectra collected while the region of tissue is in a blood-depleted state. In this embodiment, the integral of the net collected Raman spectra at the wavelength range corresponding to the analyte is divided by the integral of the net collected fluorescence spectra.

In one embodiment, the net collected Raman spectra is determined by:

$$I(\lambda)^{unp} - I(\lambda)^{pre} = \{\{(^eI_s) + (^fI_s) + (^rI_s)\} + \{(^eI_{bu}) + (^fI_{bu}) + (^rI_{bu})\}\} e^{-[b_{unp}]d} - \{\{(^eI_s) + (^fI_s) + (^rI_s)\} + \{(^eI_{bp}) + (^fI_{bp}) + (^rI_{bp})\}\} e^{-[b_{pre}]d}$$

where:
$I(\lambda)$=incident light intensity at wavelength $\lambda$
unp or u refers to an unpressed or blood-replete state
pre or p refers to a pressed or blood-depleted state
$(^eI_s)$=intensity of light scattered by elastic processes from skin
$(^fI_s)$=intensity of fluorescence from skin
$(^rI_s)$=intensity of Raman scattering from skin
$(^eI_b)$=intensity of light scattered by elastic processes from blood
$(^fI_b)$=intensity of fluorescence from blood
$(^rI_b)$=intensity of Raman scattering from blood
[b]d=volume of blood-related signal multiplied by the depth of the region of tissue The method can further comprise enhancing the spectra collected by performing a 61–501 point adjacent averaging smoothing operation on the net collected spectra; subtracting the smoothed spectra from the net collected spectra; and performing a 3–27 point adjacent averaging smoothing operation on the result. Preferably, the adjacent averaging smoothing operation of the first step is a 85–201 point smoothing operation, and more preferably, a 101 point smoothing operation. The adjacent averaging smoothing operation of the third step is preferably a 7 point smoothing operation.

In preferred embodiments, the light source emits light having a wavelength of about 785 nm to about 850 nm. One example of a light source is a laser.

The blood-depleted state can be achieved by tissue modulation, including by applying a tourniquet to the tissue, by pressing the tissue against a surface, or by applying an ultrasonic transducer to the region of tissue.

The invention also provides a noninvasive method of determining concentration of an analyte in blood of a subject that comprises irradiating a region of tissue of the subject with a light source; collecting Raman spectra emitted by the region of tissue at a wavelength range that corresponds to the analyte, the quantity of Raman spectra being indicative of the amount of analyte; and measuring absorption of incident light by the region of tissue, the amount of absorbed light being indicative of blood volume. The method further comprises dividing the collected Raman spectra by the amount of absorbed incident light to obtain a number proportional to the concentration of analyte per unit blood volume. The method can be performed while the region of tissue is in a blood-replete state and while the region of tissue is in a blood-depleted state. The net collected Raman spectra is divided by the net absorbed light, wherein net refers to the difference between the blood-replete and blood-depleted states.

The spectra collected can be further enhanced by the adjacent averaging smoothing operations described above. The method can further comprise irradiating the tissue with a second light source having a wavelength that corresponds to an isosbestic point for oxy-deoxyhemoglobin. The second light source can be, for example, a laser, a black body source or a light emitting diode (LED). In a preferred embodiment, the first light source has a wavelength of about 785 nm and the second light source has a wavelength of about 805 or about 808 nm.

The invention further provides a method of detecting Raman spectra emitted by irradiated tissue of a subject. The method comprises irradiating the tissue with light and collecting emitted Raman spectra while blood flow to the tissue is restricted by a tourniquet; and irradiating the tissue with light and collecting emitted Raman spectra while blood flow to the tissue is not restricted by a tourniquet. The method further comprises subtracting the spectra collected; and analyzing the positive spectra remaining after the subtraction. Preferably, the tissue is skin. The light preferably has a wavelength of about 785 nm to about 850 nm.

The invention also provides a method of modulating blood volume in a region of tissue for spectroscopic measurement comprising applying an ultrasonic transducer to the region of tissue. In one embodiment, multiple transducers are applied to the region of tissue.

BRIEF DESCRIPTION OF THE FIGURES

FIG. 2 is a plot of raw spectral counts, in ten thousands, at Raman shifts shown in wavenumbers collected from a subject while having his finger pressed against the metal plate of the apparatus (lower trace) and while the finger was not pressed against the metal plate (upper trace).

FIG. 3 shows the difference between the upper trace (unpressed) of FIG. 2 and the lower trace (pressed) of FIG. 2. The area under this curve is proportional to blood volume in the region of the fingertip probed.

DETAILED DESCRIPTION

Figure 1:
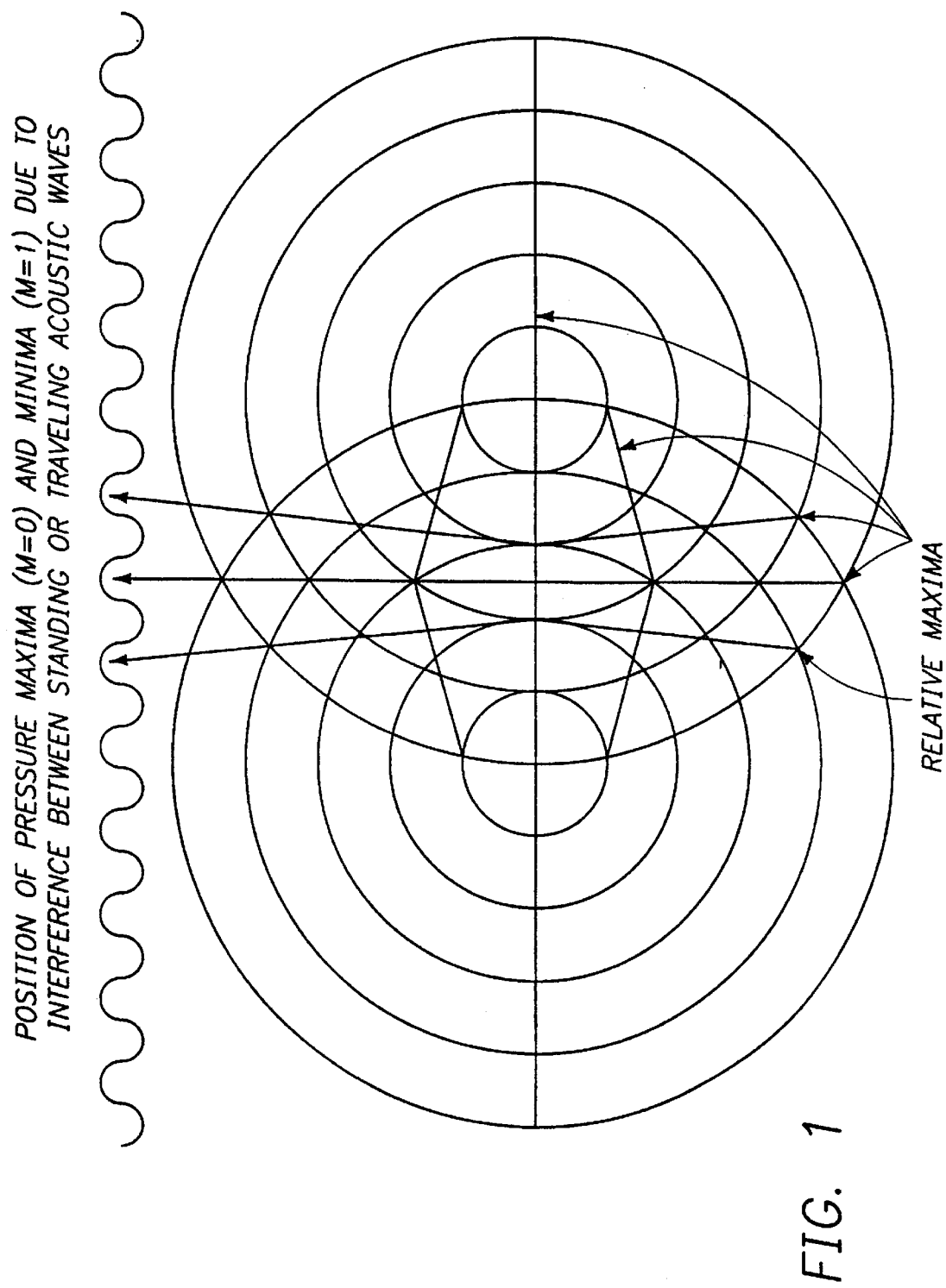
FIG. 1 is a schematic representation of tissue modulation using traveling and standing pressure wave patterns produced by interference between ultrasonic acoustic waves.

The invention provides methods for tissue modulation and for noninvasive spectroscopic analysis of mobile and immobile tissues in a subject. The invention disclosed herein is based on discovery of a mathematical algorithm for analysis of spectroscopic information relating to analytes in tissue subjected to tissue modulation. Spectroscopic measurements of the tissue can be taken while the tissue is in blood-replete and blood-depleted states that are created by tissue modulation. The methods can be used with noninvasive spectroscopy such as Raman, absorption and fluorescence, and for the analysis of various features of tissue, including skin and blood. The invention provides methods that subtract effects due to extraneous factors such as skin imperfections and residue, and that isolate information related to blood volume and to blood analytes.

The methods of the invention allow a direct subtraction of effects due to calluses, dirt, and soap residue, and other potential sources of extraneous spectroscopic signals. The method can apply to absorption, fluorescence, Raman, Rayleigh, phosphorescence, nuclear magnetic resonance, dielectric loss and other types of spectroscopy in which the interaction of matter with electromagnetic radiation can be quantitated. The method allows isolation of effects that originate from interactions of blood from those interactions involving the surrounding tissue. The method allows temporal and spatial modulation of the spectroscopic signals thereby improving the signal to noise ratio of the measurement.

Definitions

All scientific and technical terms used in this application have meanings commonly used in the art unless otherwise specified. As used in this application, the following words or phrases have the meanings specified.

As used herein, "tissue" means any portion of an organ or system of the body, including, but not limited to, skin, capillary beds, blood, muscle, breast and brain.

As used herein, "Raman spectra associated with" a given component refers to those emitted Raman spectra that one skilled in the art would attribute to that component. One can determine which Raman spectra are attributable to a given component by irradiating that component in a relatively pure form, and collecting and analyzing the Raman spectra emitted by the component in the relative absence of other components. Those skilled in the art are aware of available libraries that catalog known Raman spectra.

As used herein, "blood-replete" refers to a state in which blood content through a tissue is unobstructed by, for example, vasoconstriction induced by cooling or the application of pressure. The blood replete state can be enhanced by conditions that increase vasodilatation, such as warming.

As used herein, "blood-depleted" refers to a state in which blood flow into a tissue is restricted and blood content is minimized. A blood depleted state can be achieved by, for example, cooling and/or applying pressure to the tissue, or by controlling blood flow into and out of tissue through the use of a tourniquet.

As used herein, "region of tissue" refers to an area of tissue that light penetrates, and from which a signal is collected.

As used herein, "pressed" refers to an area of tissue to which external pressure is applied.

As used herein, "unpressed" refers to an area of tissue that has no external source of pressure applied to it.

As used herein, unless context clearly indicates otherwise, "a" means at least one, and can include a plurality.

Tissue Modulation

Whenever spectroscopy is used to analyze a chemical sample, systematic variation of the conditions of a measurement results in several types of variation of the spectroscopic signal, e.g. emission intensity, absorption strength. Modulation is often systematically applied to localize and control the spatial and temporal characteristics of the spectroscopic signals. There can be considerable variation in how one can accomplish modulation with different types of samples. For example, one cannot manipulate a living sample in the same way one can handle an inanimate object. Therefore, the types and means of modulation available to the spectroscopist are different.

Even within the realm of in vivo samples, there are different kinds of tissues, each having its own physical characteristics, e.g. optical constants, requiring different approaches to modulation. To perform spectroscopic analysis, it is first necessary to contact the target tissue with electromagnetic radiation, then to detect some aspect of the radiation or the tissue after the interaction. To the extent one wishes to probe tissues that are not on the surface of the skin, the irradiated region and surrounding tissues must be sufficiently transparent. If the analysis requires sampling of the radiation after the interaction, then the effects associated with the surrounding tissues, if any, must be considered. Given these general considerations, noninvasive spectroscopic blood analysis targets the most copious pool of blood possible that resides as near to the surface of the skin as possible.

The optics of skin influence such analyses. The outermost surface of the skin is called the stratum corneum and it consists of a layer of partially polymerized dead skin, which is ca. 10 microns thick. This layer terminates in contact with a 200 micron thick layer of living cells called the epidermis. The epidermis terminates in contact with another layer called the dermis. This is the deepest layer of the skin and it extends downward until it contacts the connective tissues, adipose tissue and muscle tissue, etc. The capillary bed is situated at the interface between the dermis and the epidermis. It consists of a plurality of high surface area structures, i.e. loops, corkscrews, switchbacks, designed to facilitate the exchange of heat and oxygen between the blood in the capillaries and the tissues at the dermis-epidermis boundary.

The tortuousity of the vascular system at this spatial scale makes it difficult to calculate the volume of the blood in an irradiated region of skin. It is desirable to know this volume because this blood is most amenable to spectroscopic study.

Although they are not equal, the real part of the index of refraction of each of the three layers of the skin is equal to between 1.34 and 1.55. Given that all of the tissues in question have a chemical composition of about 97% water, this is not very surprising. Because of the chemical and physical organization of the epidermis and the dermis, i.e. consisting of collagen and elastin fibers imbedded in a matrix of living cells, melanin-containing granules and interstitial fluids, the optics of the skin is dominated by Mie scattering. This means that most incident light with wavelength greater than about 600 nm is elastically scattered off of objects of similar size, i.e. without any wavelength shift, and with a spatial preference in the forward direction. With regard to net penetration of radiation into and out of skin, i.e. epidermis, 37% of incident radiation with 600 nm wavelength penetrates a 600 $\mu$m thick section. Most of the absorption of light, i.e. via the imaginary parts of the indices of refraction, occurs by melanin and to a lesser extent, hemoglobin.

Given the optics and structure of skin, and the need to discover a means for imposing modulation on the spectroscopic examination of capillary blood, the invention provides a number of methods for tissue modulation. The underlying strategy is to change the blood volume of a region so that spectroscopic measurements can be made with a minimum or a maximum of blood volume present. Subtraction of signals corresponding to a minimum of blood present, from those corresponding to a maximum of blood present, allows isolation of the signal associated with the blood. The invention relates to the use of various means to manipulate and thereby modulate, temporally and spatially, the blood content of a selected portion of capillary bed, and methods of isolating the signal associated with the blood.

The simplest means for tissue modulation includes using temperature and mechanical pressure, either by themselves or in concert, to control the blood content of a target capillary bed. Thermally induced vasoconstriction and vasodilatation are natural means for tissue modulation. Cooling the skin causes the associated capillaries to constrict, thereby squeezing the blood out of the cooled region. Warming the skin causes the capillaries to dilate and become flooded with blood.

Similarly, it is possible to squeeze a region of skin and observe the region to appear less pink, corresponding to the removal of blood from the squeezed region. It is possible to make spectroscopic measurements when the tissue is cooled and/or squeezed. These measurements are then subtracted from identical measurements executed when the tissue is either warmed and/or uncompressed. The difference between the two measurements is due to the changing blood content of the probed region.

Mechanical pressure can be applied in different ways with varying advantages and disadvantages for each approach. A very direct approach is for a person to press the finger tip, i.e. the fleshy side opposite the fingernail, against a clear substrate. Simply looking through a glass substrate, one can regulate the pressure so that a white region is visible where the skin is in contact with the glass, indicative of having driven the blood out of the pressurized region. It is easy to make a region uniformly white. This approach is advantageous in its simplicity and the absence of very specialized apparatus. It may be disadvantageous in that the spectroscopic probing of the tissue must occur through the glass substrate making it possible, depending on the type of spectroscopic measurement being conducted, that some type of background signal from the glass may also be unavoidable. Such problems are avoided by using a substrate having a hole that is smaller than the fingertip. The finger is pressed against the surface over the hole so as to modulate blood content in the tissue without interfering optically with the exposed surface of the fingertip.

Since this approach requires the spectroscopist to make a steady state measurement on the capillary bed in either the pressed or blood-depleted condition, it corresponds to the lowest frequency modulation. The result of subtracting the steady-state measurement on the pressed, i.e. relatively empty capillary bed, from the steady-state measurement obtained on the blood filled capillary bed, gives the lowest frequency modulation possible, i.e. 0 Hz, the DC signal.

Methods of the Invention

The invention provides methods for noninvasively measuring blood volume and analyte concentration and for obtaining spectroscopic information relating to immobile tissues, such as skin. In one embodiment, the invention provides a noninvasive method of determining concentration of an analyte in blood of a subject. The subject is preferably a vertebrate, such as a mammal, bird, reptile or fish. Examples of mammals include, but are not limited to, human, bovine, porcine, ovine, murine, equine, canine, and feline. In a preferred embodiment, the subject is human.

Examples of analytes include, but are not limited to, glucose, urea, creatinine, total protein, free fatty acids, monoglycerides, diglycerides, triglycerides, creatinine, alpha helix exposed exchangeable protein associated amide protons, cholesterol, pyruvate, tyrosine, tryptophan, bicarbonate, electrolytes, lactic acid, drugs and blood gases such as $O_2$, $CO_2$ and NO. Preferably, the analyte is glucose.

The method comprises irradiating a region of tissue, such as a fingertip, of the subject with a light source; collecting fluorescence spectra emitted by the region of tissue, the quantity of fluorescence spectra being indicative of blood volume; and collecting Raman spectra emitted by the region of tissue at a wavelength range that corresponds to the analyte, the quantity of Raman spectra being indicative of the amount of analyte. The collected spectra are then wavelength-resolved. The method further comprises dividing the collected Raman spectra by the collected fluorescence spectra to obtain the concentration of analyte per unit blood volume.

In a preferred embodiment, the fluorescence and Raman spectra are collected while the region of tissue is in a blood-replete state and collected while the region of tissue is in a blood-depleted state. The method further comprises determining the integral of net collected spectra, net collected spectra being a difference between spectra collected while the region of tissue is in a blood-replete state and spectra collected while the region of tissue is in a blood-depleted state. In this embodiment, the integral of the net collected Raman spectra at the wavelength range corresponding to the analyte is divided by the integral of the net collected fluorescence spectra.

In one embodiment, the net collected Raman spectra is determined by:

$$I(\lambda)^{unp} - I(\lambda)^{pre} = \{\{(^eI_s) + (^fI_s) + (^rI_s)\} + \{(^eI_{bu}) + (^fI_{bu}) + (^rI_{bu})\}\} e^{-[b_{unp}]d} - \{\{(^eI_s) + (^fI_s) + (^rI_s)\} + \{(^eI_{bp}) + (^fI_{bp}) + (^rI_{bp})\}\} e^{-[b_{pre}]d}$$

where:
$I(\lambda)$=collected light intensity at wavelength $\lambda$
unp or u refers to an unpressed or blood-replete state
pre or p refers to a pressed or blood-depleted state
$(^eI_s)$=intensity of light scattered by elastic processes from skin
$(^fI_s)$=intensity of fluorescence from skin
$(^rI_s)$=intensity of Raman scattering from skin
$(^eI_b)$=intensity of light scattered by elastic processes from blood
$(^fI_b)$=intensity of fluorescence from blood
$(^rI_b)$=intensity of Raman scattering from blood
[b]=concentration of hemoglobin
d=depth beneath air-stratum corneum interface from where $I(\lambda)$ originates The method can further comprise enhancing the spectra collected by performing a 61–501 point adjacent averaging smoothing operation on the net collected spectra; subtracting the smoothed spectra from the net collected spectra; and performing a 3–27 point adjacent averaging smoothing operation on the result. Preferably, the adjacent averaging smoothing operation of the first step is a 85–201 point smoothing operation, and more preferably, a 101 point smoothing operation. The adjacent averaging smoothing operation of the third step is preferably a 7 point smoothing operation.

In preferred embodiments, the light source emits light having a wavelength of about 785 nm to about 850 nm. A wavelength of 785 nm provides optimal overlap with sensitivity curve of the currently preferred silicon CCD array detector. 805 and 808 nm are desirable because these wavelengths are absorbed equally by oxy- and deoxy-hemoglobin. 808 nm is convenient for making the diode. One example of a light source is a laser. Examples of lasers suitable for use in producing an excitation wavelength include, but are not limited to, external cavity diode lasers, dye lasers, optimal parametric oscillators, and diode pumped solid state lasers.

The blood-depleted state can be achieved by tissue modulation, including by applying a tourniquet to the tissue, by pressing the tissue against a surface, or by applying an ultrasonic transducer to the region of tissue.

The invention also provides a noninvasive method of determining concentration of an analyte in blood of a subject that comprises irradiating a region of tissue of the subject with a light source; collecting Raman spectra emitted by the region of tissue at a wavelength range that corresponds to the analyte, the quantity of Raman spectra being indicative of the amount of analyte; and measuring absorption of incident light by the region of tissue, the amount of absorbed light being indicative of blood volume. The method further comprises dividing the collected Raman spectra by the amount of absorbed incident light to obtain the concentration of analyte per unit blood volume. The method can be performed while the region of tissue is in a blood-replete state and while the region of tissue is in a blood-depleted state. The net collected Raman spectra is divided by the net absorbed light, wherein net refers to the difference between the blood-replete and blood-depleted states.

The spectra collected can be further enhanced by the adjacent averaging smoothing operations described above. The method can further comprise irradiating the tissue with a second light source having a wavelength that corresponds to an isosbestic point for oxy-deoxyhemoglobin, such as 805 or 808 nm. The second light source can be, for example, a laser, a black body source or a light emitting diode (LED). Optionally, a filter can be used with a black body source to achieve wavelength selection. In a preferred embodiment, the first light source has a wavelength of about 785 nm and the second light source has a wavelength of about 805 or about 808 nm.

The invention further provides a method of detecting Raman spectra emitted by irradiated tissue of a subject. The method comprises irradiating the tissue with light and collecting emitted Raman spectra while blood flow to the tissue is restricted by a tourniquet; and irradiating the tissue with light and collecting emitted Raman spectra while blood flow to the tissue is not restricted by a tourniquet. The method further comprises subtracting the spectra collected; and analyzing the positive spectra remaining after the subtraction. Preferably, the tissue is skin. Other tissues can be used, such as ear lobe, muscle, breast or brain. The light preferably has a wavelength of about 785 nm to about 850 nm.

The invention also provides a method of modulating blood volume in a region of tissue for spectroscopic measurement comprising applying an ultrasonic transducer to the region of tissue. In one embodiment, multiple transducers are applied to the region of tissue.

EXAMPLES

The following examples are presented to illustrate the present invention and to assist one of ordinary skill in making and using the same. The example is not intended in any way to otherwise limit the scope of the invention.

Example 1
Analysis of Spectroscopic Data Related to Analytes Whose Signal is Not Absorbed by Blood This Example describes an algorithm for use in analyzing data collected using the noninvasive methods of the invention. The algorithm is applicable to methods employing tissue modulation to achieve blood-replete and blood-depleted states. Spectra are collected in both the blood-replete and blood-depleted states so that information about the volume of blood probed can be obtained. Likewise, tissue modulation facilitates analysis of components present in the blood. The algorithm of this Example is particularly suited for conditions in which the blood does not absorb the signal associated with the analyte of interest.

Let $S_{\gamma\lambda}(M)$ represent a measured value for some spectroscopic quantity indicative of the presence of a component or analyte $\gamma$, e.g. glucose.

$S_{\gamma\lambda}(M)$ is proportional to the measured absorption at a given wavelength $\lambda$, the scattered intensity of light at wavelength $\lambda$, the intensity of fluorescence at wavelength $\lambda$ or other relevant measure. $B_{65\beta}(M)$ represents total volume of blood measured in an area probed (e.g., hematocrit).

M is the fraction of the total normal blood volume that is present in the spatial region probed when $S_{\gamma\lambda}(M)$ is measured. Thus, M can vary between 0 and 1.0 and the object of tissue modulation is to manipulate the value of M.

$B_{\gamma\beta}(M)$ and $S_{\gamma\lambda}(M)$ are assigned the value of a spectroscopic measurement that is proportional to the volume of blood in the region probed. The spatial region and relative timing of the $B_{\gamma\beta}(M)$ and $S_{\gamma\lambda}(M)$ measurements are chosen to allow both measurements to be deterministically and quantitatively associated to the same blood volume. The objective is to obtain a consistent relationship between the volumes of blood and of analyte. They need not be measured at the same wavelengths since they need not be associated with the same kind of measurement. For example, $S_{\gamma\lambda}(M)$ could be associated with a Raman spectroscopic measurement and $B_{\gamma\beta}(M)$ could be absorption based. Small amounts of nonlinearity can be tolerated between the spectroscopic measurements and the concentration or blood volume so long as the dependencies can be parameterized.

Given the measurements, it is possible to measure relative variation in the blood concentration of the component $\gamma$. To begin, equation (1) is used to associate the B measurements with the volume of blood present in the probed region.

$$B_{\gamma\beta}(1) - B_{\gamma\beta}(0) = K'\beta \qquad (1)$$

The actual volume of blood, $\beta$ (in units of cc or hematocrit), is proportional to the difference between the measurements $B_{\gamma\beta}$ in the pressurized (M~0.0) and unpressed (M~1.0) states.

Similarly, equation (2) expresses the quantity of the component $$(S_{\gamma\lambda}(1) - S_{\gamma\lambda}(0)) = K''\gamma \qquad (2),$$

for example, γ, present in the same blood volume, in terms of being proportional to the difference between the measurements $S_{\gamma\lambda}$ in the pressed (M~0.0) and unpressed (M~1.0) states.

Given these definitions, one algorithm can be stated as follows:

$$(S_{\gamma\lambda}(1)-S_{\gamma\lambda}(0))/(B_{\gamma\beta}(1)-B_{\gamma\beta}(0))=K\gamma/\beta \quad (3)$$

where K=K'/K'

The concentration has units of quantity of component γ per volume of blood present, as does γ/β. K is a proportionality constant which is a function of the sensitivities of the raw blood volume and analyte concentrations and other characteristics of the measurement processes. K is constant for a particular measurement apparatus. To the extent that the apparatus obtains a value for the blood concentration of γ, there should be little dependence of the value of K on the exact sample of tissue used.

The values of M that occur in equation (1) could be associated and obtained using the following procedure. $B_{\gamma\beta}$ (0) and $S_{\gamma\lambda}$ (0) are measured on tissue that is under appropriate external pressure to drive blood out of the region probed. $B_{\gamma\lambda}$~(1) and $S_{\gamma\lambda}$ (1) are measured on tissue that has no applied external pressure. In this case, the blood present in the region probed is mostly a function of the differential between body temperature and ambient external temperature, the distance from the heart to the capillary bed in question, and the state of vasoconstriction/dilation of the local capillary beds.

In the present example, taking the difference between the M=1 and the M=0 values for S and B above allows a direct subtraction of the spectroscopic signals associated with the surrounding tissues and foreign substances on the skin surface. Because the scheme does not contemplate a time frame in which to make the individual measurements of $S_{\gamma\lambda}$ (0) and $S_{\gamma\lambda}$ (1); and $B_{\gamma\beta}$ (0) and $B_{\gamma\beta}$ (1), this would be a 0 frequency or DC measurement. It is possible to move between the pressed (M~0.0) and unpressed (M~1.0) states, at least a few times per second, using simple manual mechanical means. This corresponds to increasing the frequency of the modulation.

In some embodiments, a DC measurement will be adequate. In the embodiments in which DC measurements are made, the need to make optical contact with the skin while simultaneously maintaining the pressed condition (M~0) for a sufficiently long duration to allow sufficient signal accumulation requires special means to accomplish tissue modulation.

Example 2
High Frequency Modulation and Non-DC Current Methods

In some embodiments modulation is performed at higher frequencies due to signal to noise considerations. Higher frequency modulation allows a bandwidth reduction in the detection of spectroscopic signals that leads directly to improvement in the net signal to noise ratio. Higher frequency modulation allows for subtraction between the pressed and unpressed states in an analog fashion, with resultant improvements in signal to noise ratio. The mechanical properties of the tissue, such as the capillaries and surrounding tissues, combine with the pumping properties of the circulatory system to limit the rapidity with which one can modulate the blood contents of a particular capillary bed.

Sound waves are periodic pressure fluctuations and can be used to achieve tissue modulation for spectroscopic applications. Ultrasound has been used for a variety of biomedical applications including subdermal imaging, transdermal drug delivery, and subdermal heating therapy. In the present invention, ultrasonic waves from one or more transmitters are used to manipulate the contents of the capillary bed so that it may be spectroscopically probed using electromagnetic radiation.

In one embodiment, a single ultrasonic transducer is used, and the wave field produced in the region immediately adjacent to the transducer defines the region to be examined spectroscopically. In this case, the region of the wave field can be made more or less blood-depleted by increasing or decreasing the intensity of the ultrasound. Alternatively, simply turning the transmitter off allows blood to refill the region under normal heart beating thereby reproducing the blood-replete state.

Blood tissues are not able to respond to the ultrasonic pressure at the same frequency as the ultrasonic pressure waves/fluctuations themselves. These frequencies range from roughly $10^1$ KHz to the $10^1$ MHz range, with displacements of 0.01 to 1.0 μm and across the entire ultrasonic frequency range, mass transfer of objects as large and heavy as erythrocytes will not occur on the timescale of the pressure fluctuations of the individual waves. However, the blood fluids and cells will respond on a much slower timescale to the greater average pressure in the ultrasonically irradiated tissue as compared to the surrounding tissues. It is this average pressure difference that provides the impetus for tissue modulation. Those skilled in the art will appreciate that impedance matching and other geometrical factors will play a role in determining the most advantageous frequency range to effect tissue modulation in a particular situation.

There are additional strategies for effecting tissue modulation with a single transducer. The approach described above amounts to a "single pass" approach. The ultrasonic waves propagate away from the transducer and effect tissue modulation before they dissipate into the vast reservoir of surrounding tissues. Another approach, termed "multipass", involves using hard tissues as a "mirror" so that as waves emanate from the single transducer, they encounter other waves that previously emanated from the same transducer. Constructive and destructive interference occurs between the various reflected and emitted waves leading to production of a steady state pressure field. The spatial and temporal properties of the net resulting pressure field are dependent on the relative phase, amplitudes and polarization of the waves. The properties of the tissue modulating field can be calculated using wavelets.

The single transducer multipass approach is particularly suited to modulating the tissues of finger tips because simple well known anatomy provides a bone within about 1 cm of the transducer. Thus, the waves propagate from the transducer, enter the tissue through the skin, propagate through the underlying tissue including the capillary bed to the bone, reflect off the bone, propagate back through the same tissue including the capillary bed and then encounter the skin. Some of the waves reflect off the skin surface and reenter the tissues with an inward propagation vector whereas the rest scatter off the skin-air interface and dissipate into all directions. The constructive and destructive interference between the reflected wave field and the incident wave field provides regions of higher and lower pressure than is achievable using the single-pass approach. The overall effect is that the average net pressure is greater than that obtained in a single pass, thus improving the efficiency of the tissue modulation.

The wavelength of the ultrasound ranges from a fraction of a millimeter to a few millimeters and to a certain extent this defines the size of the region that can be tissue modulated. The size of the glow-ball produced in tissue by a moderately focussed near infrared laser is on the order of 100 µm to 2 mm depending on the wavelength, and to some extent this defines the size of the region which requires tissue modulation. Properties of the light collection system are also important in this respect.

The exact locations where constructive and destructive interference occur will vary somewhat, i.e. "smear", if the factors which determine wavelength, phase and amplitude vary during the course of applying the ultrasound. Relative motion of the soft and hard tissues, with respect to each other as well to the transducer(s), as well as tissue density fluctuations could smear out the interference over regions larger than the wavelength of the acoustic radiation. The necessity is to spectroscopically probe a region that is larger than the wavelength of the ultrasound. Ultrasound is used to transform that region from a blood-replete region to a blood-depleted region. Smearing can be useful because it can give a more homogeneously modulated region for spectroscopic interrogation. The smearing effect will also tend to decrease the steady state pressure differences that can be attained so the practitioner will not overly encourage smearing.

A preferred embodiment provides the use of ultrasonic transducers to propagate sound waves into a chosen capillary bed such that standing and traveling wave patterns occur. The waves produce the appropriate tissue modulation. This modulation can be established in spatially and temporally advantageous patterns due to considerable latitude in choices of wavelength, polarization, and amplitude of the ultrasonic waves. Hard tissues such as bones in the vicinity of the chosen capillary bed can act like a mirror in setting up interference patterns that can be exploited in other tissue modulation schemes.

In other embodiments, multiple transducers or transmitters can be incorporated. The multiple transducer approach resembles the single transducer-multipass approach in that interference is used to achieve greater temporal and spatial control of the tissue modulation pattern. Multiple transducers can be used to generate additional pressure over a single transducer. Because transducers can be produced in various shapes and with various polarization, those skilled in the art will appreciate that there is considerable latitude in designing particular elements of an ultrasonic tissue modulator. The shape of the orifice used in current tissue modulator prototypes can also determine the spatial pattern for deploying the ultrasonic transducers.

FIG. 1 is a schematic representation of tissue modulation using traveling and standing pressure wave patterns produced by interference between ultrasonic acoustic waves.

Example 3
Analysis of Spectroscopic Data by Compensating for Effect of Blood Content on Analyte Signal This Example describes another algorithm for use in analyzing data collected using the noninvasive methods of the invention. This algorithm is also applicable to methods employing tissue modulation to achieve blood-replete and blood-depleted states. Spectra are collected in both the blood-replete and blood-depleted states so that information about the volume of blood probed can be obtained. Likewise, tissue modulation facilitates analysis of components present in the blood. The algorithm of this Example is particularly suited for conditions in which the blood absorbs some of the signal associated with the analyte of interest, and compensates for the effects of this absorption on the analyte-related signal.

Rationale

The use of Raman spectroscopy to gather information from living tissues requires minimizing the entry of directly reflected light into the collection system. When a focused beam of 785 nm light impinges onto the surface of skin, a certain amount, about 5–10% of the total, reflects directly off without penetrating the skin sufficiently to bear information regarding the chemical nature of the underlying tissues. Since the air-skin interface occurs outside of the capillary beds, the degree to which the capillaries are blood-filled or depleted has no bearing on the intensity of the directly reflected light that reaches the detector. The smallest practically attainable fraction of the directly reflected light, even with the most strenuous efforts to exclude such light, will be orders of magnitude more intense than even the fluorescence, and the Raman intensity is smaller still. Thus, the collection of directly reflected light is minimized as much as possible.

As the incident light propagates into the tissues, it encounters objects on the order of the wavelength of the light and the light undergoes Mie scattering. Mie scattering is an elastic process that has a strong preference for producing a scattered wave in the forward direction. Empirically, it is known that a "glow ball" of light is formed that is well represented as if the light propagates as in a random walk once it penetrates the first micron or so of the stratum corneum. This process involves, and results in, no wavelength shift for the scattered radiation. Rayleigh scattered light and the Mie scattered light can be differentiated on the basis of the much stronger preference for forward angles of the Mie process. There are various other elastic processes/scattering centers that occur but all, by the definition of elastic, do not result in wavelength shifted scattered light.

This leaves inelastic processes, at least two of which are certainly important. The first is fluorescence and the second is Raman scattering. Both have similar angular dependencies on the incident light with both being much more isotropic than the Mie process. The amount, i.e. parameterization, of fluorescence is proportional to the intensity of the incident light, the absorption strength, the concentration of the absorber and the quantum yield for emitting fluorescence. Raman scattering intensity can be parameterized in terms of the concentration of scattering centers, the cross-section for scattering with a particular wavelength shift, and the intensity of the incident exciting radiation. Fluorescence is fundamentally a broadband emission producing light having a relatively smooth spectral distribution spread over at least $10^1$ to $10^2$ nanometers. In contrast, Raman scattering is typically spread over a narrow range of wavelengths (about 50 $cm^{-1}$ at 785 nm).

Components of Algorithm

Thus, one can list all sources of radiation that could reach the detector when intense, narrow spectral bandwidth light is focused onto the surface of a finger tip: 1) contributions to the unwavelength-shifted intensity due to Mie-Rayleigh scattering, i.e. net all elastic processes from either skin or blood, ($^eI_{s,b}$; 2) contributions to the wavelength-shifted intensity due to fluorescence ($^fI_{s,b}$) from either skin or blood; and 3) contributions to the wavelength-shifted intensity due to Raman scattering ($^rI_{s,b}$) from either skin or blood. "Skin", in this context, means all stationary (immobile) tissues including bone, connective tissues and all other materials which do not move under application of external pressure, as with tissue modulation.

The incident light arriving at the tissue to be probed can be viewed as the interaction of a narrow, converging pencil of rays with the skin and underlying tissues. From each volume element, perhaps from each disk of varying depth produced by subdividing the total interaction volume with a slice perpendicular to the direction of propagation of the incident light, where the incident intensity is sufficient to produce observable emission, one can enumerate the various sources of light stimulated by the incident light. Initially, the intensity of the elastically and inelastically scattered light, and the fluorescence can be represented as a sum of terms:

$$I \sim (^eI_{s,b}) + (^fI_{s,b}) + (^rI_{s,b}) = \{(^eI_s) + (^rI_s)\} + \{(^eI_b) + (^fI_b) + (^rI_b)\}$$

Each volume element so defined will experience a different incident intensity ($I_o$=incident intensity (in photons/(sec-cm$^2$) or W/cm$^2$) at $\lambda_o$) due to absorption and scattering processes. It is possible to represent the intensity as a function of depth in terms of equation 0. Here d is the depth and [b,s] represents an effective "concentration" for the skin and blood between the volume element under examination and the set of points where light emanating from that element would have to leave the body in question to enter the light collection system.

$$I(d) = I_o e^{-[b,s]d} \qquad (0)$$

Each contribution to the intensity can be represented, i.e. parameterized, as follows:

$$(^eI_{s,b}) \sim I_o[s]^e\sigma_s + I_o[b]^e\sigma_b$$

$$(^fI_{s,b}) \sim I_o[s]\Gamma_s + I_o[b]\Gamma_b$$

$$(^rI_{s,b}) \sim I_o[s]^r\sigma_s + I_o[b]^r\sigma_b$$

where:

$I_o$=incident intensity at $\lambda_o$

[s]=concentration/ molarity of "skin" integrated over effective "glow-ball" (i.e. per volume element)

[b]=concentration/ molarity of "blood" integrated over effective "glow-ball" (i.e. per volume element)

$^e\sigma_b$=cross-section per mole for elastic scattering of $I_o$ by blood $^e\sigma_s$=cross-section per mole for elastic scattering of $I_o$ by skin $\Gamma_s$=quantum yield for fluorescence for skin (includes absorption coefficient)

$\Gamma_b$=quantum yield for fluorescence for blood (includes absorption coefficient)

$^r\sigma_s$=cross-section per mole for Raman scattering of $I_o$ by skin $^r\sigma_b$=cross-section per mole for Raman scattering of $I_o$ by blood.

The total amount of scattered/fluorescence light is around a factor of two to three orders of magnitude diminished from $I_o$ so any so-called "stimulated" Raman effects (dependent on Raman scattered light not from $I_o$ but from Raman scattered light from $I_o$) can be ignored. Across the near infrared spectral region, the depth of penetration is such that it is possible to image to $10^2$–$10^3$ microns below the surface of the stratum corneum and so, based on numbers from Anderson and Parrish, in excess of 80% of the incident light is expected to be present in an interaction volume (i.e. disk diameter) comparable to the incident spot size at e.g. $\lambda_o$=785 nm. Thus, approaching 40% of the total Raman scattered radiation originates from ~$10^2$ microns beneath the surface if one includes the loss (absorption by the blood or tissues/ deflection from the collection cone by Mie scattering, etc.) of Raman scattered intensity before it emanates from the interaction volume into the collection cone of the observation system.

Fluorescence-Based Measurement of Blood Volume

To most fully, but simply, represent the situation obtained using mechanical pressure induced tissue modulation, one can assume that, in the near infrared spectral range, the vast majority of absorption of all light is by the blood. At this point, the quantity [b] includes all possible blood-borne chromophores and scattering centers.

[b]=[oxyhemoglobin]+[deoxyhemoglobin]+[carotenoid species]+ [others]

[s]=[keratin]+[interstitial fluid]+[lipids]+[ceramides]+[others]

Furthermore, since the chromophore, e.g. oxyhemoglobin/deoxyhemoglobin is a large molecule and the transition is electronic/vibronic, all absorption is broad-band and related to the strength and features of the fluorescence as well. Thus, emission from a volume element at a particular depth that is not under any external tissue modulating stimulus is diminished using (following St. Jacques or Anderson and Parrish) the Beer's Law inspired exponential:

$$I(d) \sim \{\{(^eI_s) + (^fI_s) + (^rI_s)\} + \{(^eI_b) + (^fI_b) + (^rI_b)\}\} e^{-[b,s]d}$$

The reference to skin and a particular depth will be left out of what follows because of the assumption and because the emission is from a single volume element. One could integrate the intensity over all volume elements at the end of this calculation to obtain the total emission from the interaction volume. This integrated emission would be proportional to the total amount of material in the integrated volume. To obtain concentrations, the integrated intensity must be normalized to the tissue volume probed.

$$I \sim \{\{(^eI_s) + (^fI_s) + (^rI_s)\} + \{(^eI_b) + (^fI_b) + (^rI_b)\}\} e^{-[b]d} \qquad (1)$$

Equation 1 would correspond to the expected emission from a volume element in which the tissue can be considered "blood replete". This in turn corresponds to the situation which prevails when a Raman spectrum is taken from a finger tip in the current tissue modulator in the "unpressed" condition. The blood content in the interaction volume can be represented as $b_{unp}$.

$$I(\lambda)^{unp} \sim \{\{(^eI_s) + (^fI_s) + (^rI_s)\} + \{(^eI_{bu}) + (^fI_{bu}) + (^rI_{bu})\}\} e^{-[b_{unp}]d} \qquad (1)$$

The pressed condition(blood content=$b_{pre}$ can be represented as:

$$I(\lambda)^{pre} \sim \{\{(^eI_s) + (^fI_s) + (^rI_s)\} + \{(^eI_{bp}) + (^fI_{bp}) + (^rI_{bp})\}\} e^{-[b_{pre}]d} \qquad (2)$$

The "tissue modulated" Raman spectrum can be represented as the difference between the equations 1 and 2.

$$I(\lambda)^{unp} - I(\lambda)^{pre} \sim \{\{(^eI_s) +$$
$$(^fI_s) + (^rI_s)\} + \{(^eI_{bu}) + (^fI_{bu}) + (^rI_{bu})\}\} e^{-[b_{unp}]d} - \{\{(^eI_s) + (^fI_s) + (^rI_s)\} +$$
$$\{(^eI_{bp}) + (^fI_{bp}) + (^rI_{bp})\}\} e^{-[b_{pre}]d} \qquad (3)$$

It is possible to continue the analysis in various ways, but for the present purposes it is useful to consider the limiting case of complete evacuation of blood (M=0; [$b_{pre}$]=0) from the interaction zone during the tissue modulation. In this case, one can write the special case for the emission at wavelength A from a single volume element as:

$$I(\lambda)^{unp} - I(\lambda)^{pre} \sim \{\{(^eI_s) + (^fI_s) + (^rI_s)\} + \{(^eI_{bu}) + (^fI_{bu}) + (^rI_{bu})\}\} e^{-[b_{unp}]d} - \{\{(^eI_s) + (^fI_s) + (^rI_s)\}\} = \{(^eI_{bu}) + (^fI_{bu}) + (^rI_{bu})\} e^{-[b_{unp}]d} + \}\}(^eI_s) + (^fI_s) + (^rI_s)\}\}(e^{-[b_{unp}]d} - 1) \quad (4)$$

All the intensities are positive definite and the arguments in the exponential are positive definite. Therefore, the skin term, i.e. the second group of terms on the right hand side, subtracts from the intensity from the blood because:

$$(e^{-[b_{unp}]d} - 1) < 0$$

Furthermore, the term:

$$\{\{(^eI_s) + (^fI_s) + (^rI_s)\}\} > \{(^eI_{bu}) + (^fI_{bu}) + (^rI_{bu})\}$$

because more incident light ($I_o$) reaches the blood and tissues when the interaction volume is blood depleted than when it is not. Thus, for conditions involving large enough modulation of the fluid components, i.e. blood, it is expected that the tissue modulated (unpressed-pressed) Raman spectrum could appear inverted, i.e. negative-going peaks. The net Raman spectrum will be the difference between the weighted spectrum of the tissue and the blood.

The inhomogeneity of the tissues and the behavior of the mobile tissues bears special consideration at this point. First, by its very nature, its location in the tissues, and purpose for existence, the most mobile tissue is the blood. The interstitial fluids are not nearly as mobile, as evidenced by the fact that the "mortar" of the stratum corneum involves organized/anchored assemblies involving solid protein, lipid and aqueous phases. (Minimally invasive diabetes procedures must "extract" the fluids for analysis, whereas a simple puncture yields freely flowing blood.) Furthermore, the regions between the "bricks" are not as large as those of the circulatory system. This is not to suggest that interstitial fluids are immobile, but to reinforce the notion that the blood is much more mobile. The tissue modulated spectrum of mobile components will therefore be enriched in the spectrum of blood compared to interstitial fluid.

The spectrum produced by Raman scattering in the stratum corneum and the upper epidermis itself, i.e. all tissues from the upper edge of the shallowest capillary bed to the surface of the stratum corneum, is not affected by the presence or absence of blood. This can be seen by integrating equation 4 over the interval, 0<d<approximately 150–200 μm. Raman scattered light can enter the collection cone without traversing any capillary bed and so the contribution this region makes to spectra of both blood-depleted and blood-replete finger tips will be substantially eliminated by subtraction of pressed from unpressed conditions. This is not the case for deeper tissues that are at or below the capillary bed and whose emission, which actually arrives at the skin surface, has been substantially filtered by the local blood supply.

By varying the magnitude of the $e^{-[b_{unp}]d}$ term, i.e. the greater the blood content the smaller the exponential, and making assumptions about the relative magnitude of the Raman cross-sections for blood components versus skin components, it is possible to see that at some point the spectrum becomes enriched in either the skin or blood related features. For essentially equal Raman cross-sections (an assumption), when the blood is a major absorber, e.g., $e^{-[b_{unp}]d} = 0.2$ or less corresponding to 20% transmittance over the effective path length of d, the net spectrum becomes enriched in blood/mobile tissue features. It is clear that given the relative cross-sections for the blood and skin related features, there will be a preferred degree of tissue modulation that can isolate as much of the spectrum of either the blood or the skin as possible. It will be possible to obtain even better isolation by measuring tissue modulated spectra over a range of independently measured $e^{-[b_{unp}]d}$ values, i.e. blood volumes or degrees of modulation, and fitting the variation to equation 3.

Absorption-Based Measurements of Blood Volume

For the purpose of obtaining a blood volume, sometimes it will be useful to perform independent measurement of some component of [b] using an absorption approach as in pulse oximetry. The closest approach to the situation embodied by equation 4 occurs using a tourniquet at the base of the finger in question. In this case the finger can be seen to blanch deeper white than during any squeezing and unsqueezing experiment. This direct visual observation, and other experiments measuring the transmittance of a near infrared laser (805 nm, 830 nm, 980 nm) through the finger under pressed and unpressed conditions, with and without the tourniquet, shows that there is very little blood in the finger tip area at all when the tourniquet is in place. (Very little if any modulation can be observed with pressing and unpressing and no pulse can be observed.) In this case, the spectrum obtained by subtracting the tourniqueted finger spectrum from the untourniqueted (and not pressed in any way) finger does in fact have all negative-going Raman features as predicted. What blood there may be in the tourniqueted finger would appear to reside in the more major blood vessels which exist deeper in the finger near the bone. The capillary bed appears nearly empty, and this virtually eliminates absorption effects by blood.

On the other hand, as indicated using direct visual observation and the same type of diode laser absorption measurements, using only pressing and unpressing, the modulation appears to be much less deep, i.e. less blood moved in and out. Based on equation 4, it is clear that the blood spectrum is best isolated when the modulation is not deep. That is, if the term $(e^{-[b_{unp}]d} - e^{-[b_{pre}]d})$ is not too large, but corresponding to 0<M<1, then the filtered Raman spectrum of blood will exceed that of the skin and the resultant (unpressed-pressed) will be positive-going and substantially more representative of blood (i.e. mobile tissues) than of the skin. This was observed for nearly all of our pressing/unpressing/orifice based tissue modulation experiments.

Given the opposing tendencies revealed by the extreme situation represented by equation 4 (M=0), it will be preferable to be able to reproducibly obtain optimal and precisely measured modulation depths for noninvasive blood analysis using Raman scattering or any other spectroscopic probe. In addition, to obtain maximum isolation of blood-based Raman features, it is preferable to obtain a modulated blood volume measurement simultaneously with the Raman so that concentrations of blood analytes can be calculated. To obtain concentration, there are two unknowns to determine experimentally: a measure of the analyte of interest and a measure of the volume of blood containing that amount of analyte. This can be accomplished in a number of ways, but the measurement of blood volume is preferably independent of the Raman measurement. This feature allows transferability of the instrument from person to person. Routine recalibration can be performed as required.

First, in analogy with pulse oximetry, one can inject light at the wavelength of an isosbestic point for hemoglobin (805 nm) into the volume in question and measure how much is remitted. The more light that is remitted, the less blood was in the volume in question. This can be represented as follows. If light of wavelength $\lambda_i$ impinges on the volume in question, some will enter the volume. By a random walk trajectory, some of the light will remit (re-emerge) from the interaction volume and the amount that does will be representative of the amount of blood (i.e. absorber(s)) within the volume. By choosing the wavelength of an isosbestic point, the absorption measurement, which is taken to be a measure of blood volume, is independent of the degree of oxygenation of the blood. The degree of oxygenation is changing over the course of the Raman measurement, so another wavelength could be used. The blood volume measurement would then be averaged over many heart pulse cycles and, if there were any unusual variations in blood oxygen, then the blood volume measurement could be affected. Using an isosbestic point wavelength eliminates this possibility.

One issue in this approach involves the overlap between the interaction volume corresponding to the Raman measurement with the interaction volume corresponding to the blood volume measurement. Different wavelengths have different penetration depths and, without assuming the use of confocal techniques to obtain depth resolution, there is no guarantee that the scattering volume will exactly correspond to the volume over which the blood content is obtained. However, if the ratio of volumes is constant, then the concentrations obtained will be in the same constant proportion to the true concentrations. Given appropriate internal calibration, compensation and stability of the data collection system, the proportionality will remain constant.

Integrating the M=0 limiting case represented by 4 over the distribution of depth elements associated with the shape of the glow ball provides a more detailed model of a tissue modulated Raman spectrum.

$$I(\lambda)^{unp} - I(\lambda)^{pre} = \{(^eI_{bu}) + (^fI_{bu}) + (^rI_{bu})\}e^{-[b_{unp}]} + \quad (5)$$
$$\{(^eI_s) + (^fI_s) + (^rI_s)\}(e^{-[b_{unp}]} - 1)$$
$$= \{(I_0[b]^e\sigma_b) + (I_0[b]\Gamma_b) +$$
$$(I_0[b]^r\sigma_b)\}e^{-[b_{unp}]} + \{(I_0[s]^e\sigma_s) +$$
$$(I_0[s]\Gamma_s) + (I_0[s]^r\sigma_s)\}(e^{-[b_{unp}]} - 1)$$
$$= I_0\{[b]\{^e\sigma_b + \Gamma_b + {}^r\sigma_b\}e^{-[b_{unp}]d} +$$
$$\{[s]\{^e\sigma_s + \Gamma_s + {}^r\sigma_s\}\}(e^{-[b_{unp}]d} - 1)\}$$

To arrive at 5, the depth of the volume element in question is introduced in all the exponentials corresponding to the absorption of the light emanating from each volume element. Also included are the definitions of all the sources of wavelength shifted and Rayleigh scattered light in terms of cross-sections, concentrations and quantum yields (which includes absorption strengths). It is possible to obtain values for $e^{-[b_{unp}]d}$, [b], [s], the cross-sections and effective quantum yields based on empirical calibrations. Including the absorption of the light incident on the volume element leads to equation 6.

$$=I_0e^{-[b,s]d}\{[b]\{^e\sigma_b+\Gamma_b+{}^r\sigma_b\}e^{-b[b_{unp}]d}+\{[s]\{^e\sigma_s+\Gamma_s+{}^r\sigma_s\}\}(e^{-[b_{unp}]d}-1\} \quad (6)$$

Equation 6 can be averaged or integrated over the distribution of d values consistent with the dimensions of the glow-ball. In many cases this integral can be obtained in closed form but, if needed, it can always be obtained numerically. The exponential multiplying the entire sum 5 has a different wavelength dependence than do the other terms (fluorescence and scattered wavelengths) since it only applies to the incident wavelength $\lambda_o$.

To obtain a measure of how much wavelength shifted light can reach the detector, the integral will be over three linear dimensions, i.e. dx,dy,dz or the equivalent in whatever coordinates are convenient (perhaps d,θ,φ) and so will introduce a term corresponding to:

$$l^3=\text{volume}$$

To see this more clearly, tissue modulated Raman spectrum(a spectrum via the $\sigma(\lambda)$, $\Gamma(\lambda)$ terms) can be represented as:

$$\int[\text{equation 6}]dxdyds\sim[\text{equation 6}]xyz\sim[\text{equation 6}]l^3\sim[\text{equation 6}]V=\mathcal{S}(\lambda)$$

Inspection of this integral of equation 6 shows that a measured tissue modulated spectrum ($\mathcal{S}$) is proportional to the total amount of each substance in the interaction volume, V. It contains a sum of terms which are linear in concentrations, i.e. [b] and [s], and do not contain the integration variable. Thus, when the integral over the interaction volume is performed explicitly, equation 6 is independent of two of the integration variables.

The only terms in equation 6 which contain the remaining variable to be integrated over d, or its mapping onto x, y, z, are the exponentials. These terms produce an exponential weighting which diminishes the contribution of deeper tissues relative to shallower tissues. A Taylor series expansion of the exponential has a leading term linear in d which, for small d, contributes to the weighting. Thus, to a first order approximation, [b]V=moles. When the independent blood volume is measured, a value V' will be obtained. V' need not be exactly equal to V so long as it overlaps the analyte interaction volume substantially and thereby does in fact sample the environment responsible for the other [b] analyte related signals. It is particularly advantageous for V' to be measured using a $\lambda$ having similar penetration characteristics as that used to obtain a signal for the analyte [b]. As will be shown below, this leads to a better cancellation of deviations from the Taylor series expansion.

It is assumed for the moment that it is possible to identify a scattering wavelength, $\lambda_g$, which can be associated with a particular analyte, e.g. glucose. Equation 6 is completely general in that the Raman cross-section can be chosen to correspond to a particular analyte [b]. To obtain concentrations, i.e. an expression in terms of measurable quantities for [b], the integral of $\mathcal{S}(\lambda)$ is divided over a suitable interval containing $\lambda_s$ by V'. That is:

$$\mathcal{S}/V'=[\text{equation 6}]V/V'=[\text{equation 6}]C\sim\text{constants}\{[b]+[s]\} \quad (7)$$

C represents the calibration constant associated with a particular alignment/instrument and user. So long as C is constant, corresponding to a constant degree of spatial overlap between the actual weighted volumes (blood and analyte volumes) interrogated by light, inspection of equation 6 shows that the instrument/measurement process produces a spectrum in which the integrals over scattering wavelength shift are sums of contributions each of which is proportional to concentrations of blood and tissue components, i.e. [b] and [s] respectively. In reality, of course, there may be more than one analyte contributing to the scattered intensity at any particular Raman shift but the main point is that the scattered intensity and the fluorescence intensity is proportional to the concentration of analytes.

Blood volume measurement can be conveniently made using the fluorescence of blood and tissues. A judicious choice of $\lambda_s$, say 785 nm or 805 nm, allows a convenient method for determining a blood volume, V', which can be used in 7. In this case, sufficient fluorescence is produced to allow blood volume estimation while still not obscuring the Raman features. As mentioned above, fluorescence is broadband emission whereas Raman is narrow. Thus it is easy to estimate the total fluorescence spectrum, $\mathcal{S}$, by simply smoothing out the Raman features, which in any case contribute a relatively small amount of emission compared to the fluorescence, using adjacent averaging with a wide window or other suitable means. Having thus estimated the total fluorescence from the raw data for unpressed and pressed conditions, the following quantity is obtained in the limiting case of M=0.

$$\mathcal{S}(b')=I_o e^{-[b,s]d}\{[b']\{^e\sigma_{b'}+\Gamma_{b'}\}e^{-[b_{\text{unp}}]d}+\{[s]\{^e\sigma_s+\Gamma_s\}\}(e^{-[b_{\text{unp}}]d}-1) \quad (8)$$

Similarly, it is easy to simply direct attention to wavelength shifted light and thereby remove all elastic processes yielding:

$$\mathcal{S}(b)=I_o e^{-[b,s]d}\{[b]\{\Gamma_b\}e^{-[b_{\text{unp}}]d}+[s](\Gamma_s)(e^{-[b_{\text{unp}}]d}-1)\} \quad (9)$$

Introduced into 8 is b', to emphasize that [b] can be either something that is proportional to the hematocrit, i.e. hemoglobin content, or it could be another analyte, b'. In 9 [b] is used to acknowledge that the majority of the fluorescence is known to come from the blood and the so the fluorescence is a good measure of blood volume [b]≡V', i.e. the integral of $\mathcal{S}(\lambda)$ over a wide interval in $\lambda$, is a good measure of blood volume, i.e. V'. Thus if $\mathcal{S}(b')$ is integrated over an appropriately chosen narrow range of $\lambda$ to estimate [b'] corresponding to a volume V, and $\mathcal{S}(b)$ is integrated over a wide range excluding the un-wavelength shifted light to estimate V', one can obtain:

$$\mathcal{S}(b')=\{I_o e^{-[b,s]d}\{[b']\{'\sigma_{b'}\}e^{-[b_{\text{unp}}]d}+\{[s]\{'\sigma_s\}\}(e^{-[b_{\text{unp}}]d}-1)\}/\{\{I_o e^{-[b,s]d}\{[b]\{\Gamma_b\}e^{-[b_{\text{unp}}]d}+[s](\Gamma_s)(e^{-[b_{\text{unp}}]d}-1)\}=\{[b']\{('\sigma_b)\}e^{-[b_{\text{unp}}]d}+\{[s]\{('\sigma_s)\}\}(e^{-[b_{\text{unp}}]d}-1)\}/\{[b]\{\Gamma_b\}e^{-[b_{\text{unp}}]d}+[s](\Gamma_s)(e^{-[b_{\text{unp}}]d}-1)\}$$

Thus, if one is attempting to monitor the concentration of an analyte [b']:

$$[b']V/[b]=[b']V/V'$$

Using the fluorescence as a measure of blood volume provides a first order cancellation of all penetration effects, i.e. the factor $I_o e^{-[b,s]d}$. And the factors: $(e^{-[b_{\text{unp}}]d}-1)$ and $e^{-[b_{\text{unp}}]d}$ are equal for the numerators and denominators as well because the fluorescence experiences the same propagation effects as does the Raman light because they span the same wavelength range. Similar statements can be made about the detector sensitivity and the net modulation transfer function of the optical collection and analysis system. The noise sources will be the same in many cases and will lead to a more precise and repeatable compensation.

Example 4:
Blood Analyte Measurements from Human Subjects Using Fluorescence-Based Blood Volume Determinations This Example demonstrates that the noninvasive analysis methods disclosed above can be used to obtain blood glucose measurements that very closely approximate measurements taken from the same subjects using conventional, invasive techniques. This Example also demonstrates the use of fluorescence-based blood volume determinations, as well as the enhancement of spectral information using the smoothing operations disclosed above.

Materials & Methods

The apparatus included a light source, a metal plate having a hole through which incident and emitted light could pass, a detector, and a signal processor. Suitable components and specific embodiments of the apparatus can be adapted from other Raman spectroscopy systems known in the art (see, e.g., U.S. Pat. Nos. 5,553,616; 5,510,894; 5,615,673; and 5,551,422). The edge of the hole in the metal plate was the surface against which the finger was pressed in order to modulate blood content in the tissue probed. For the data presented here, the light source was an external cavity diode laser emitting at 785 nm (SDL, Inc., Santa Clara, Calif.). The detector was a CCD array (Princeton Instruments, Trenton, N.J.). Light was collected by 250 mm f1.4 Nikon lenses. Light was first filtered by a holographic notch filter and dispersed by a holographic spectrograph (both from Kaiser Optical Systems, Ann Arbor, Mich.). Signal processing was performed with a standard personal computer.

Subjects placed a fingertip against a ¼ inch hole in an aluminum plate, alternating between pressing against the plate to achieve a blood-depleted state and releasing pressure against the plate to achieve a blood-replete state. Incident light at 785 nm was passed through the hole in the metal plate to the subject's fingertip, and collected spectra were analyzed as described below. Light was focused onto the finger with a 13 cm focal length piano convex lens. Incident laser power at the finger tip was 50 m Watts and the spectral bandwidth was approximately 1 $cm^{-1}$.

Results

FIG. 2 shows representative raw spectral counts, in ten thousands, at Raman shifts shown in wavenumbers collected from a subject while having his finger pressed against the metal plate of the apparatus dower trace) and while the finger was not pressed against the metal plate (upper trace). FIG. 3 shows the difference between the upper trace (unpressed) of FIG. 2 and the lower trace (pressed) of FIG. 2. The area under this curve is proportional to blood volume variation in the region of the fingertip probed due to tissue modulation.

Figure 4:
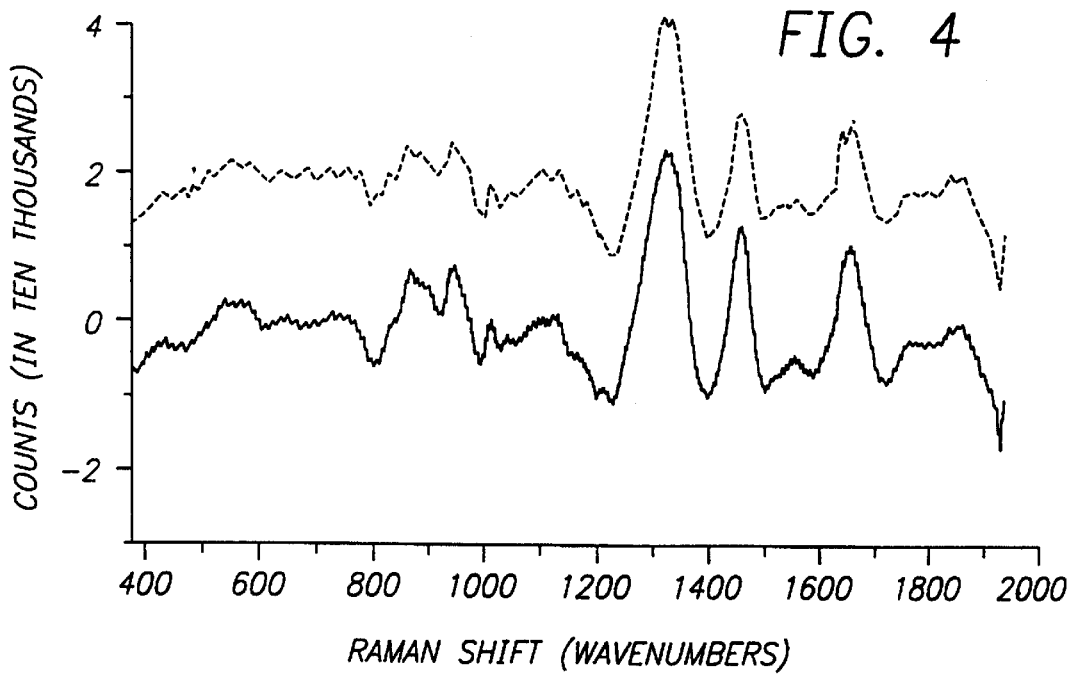
FIG. 4 is a plot generated by taking the raw data shown in FIG. 2, performing a 101 point adjacent averaging smoothing operation, then subtracting the smoothed data from the raw data, and performing a 7 point adjacent averaging smoothing operation on the result. The upper trace (unpressed condition) has been shifted upward by 20,000 counts to avoid overlapping of the displayed traces.
Figure 5:
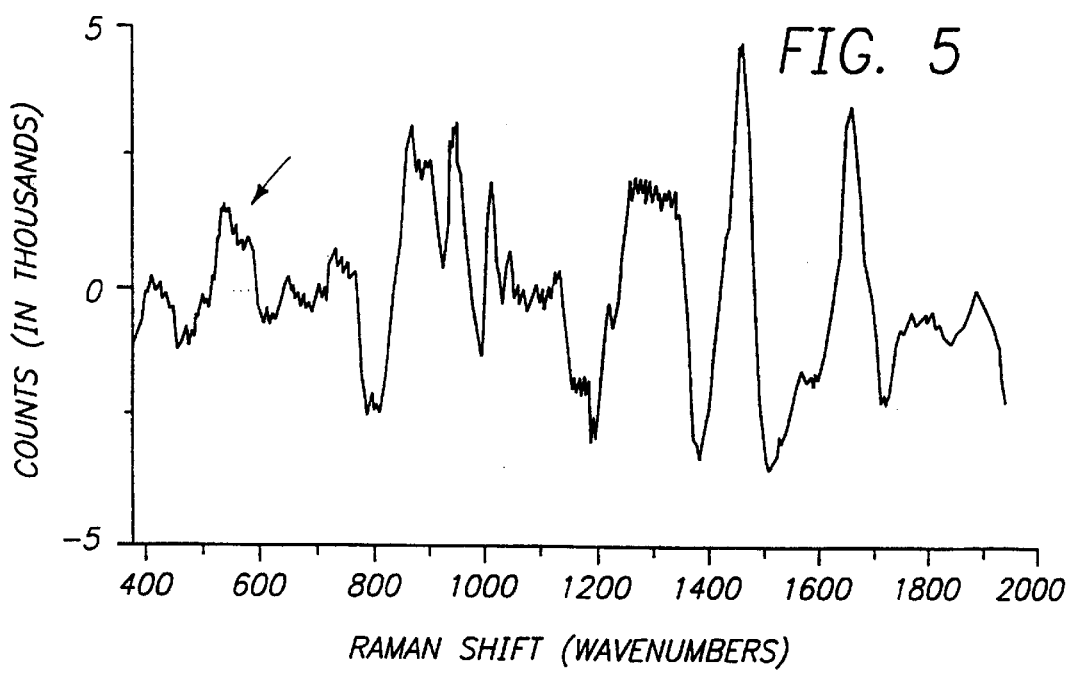
FIG. 5 shows the difference between the two traces shown in FIG. 4. This subtraction reveals Raman features attributable to blood. One can integrate the area between the curve and zero in the region between 495 and 560 wavenumbers (arrow) to obtain a measure corresponding to blood glucose content. The ratio of this value to the area under the curve shown in FIG. 4 corresponds to blood glucose concentration.

FIG. 4 is a plot generated by taking the raw data shown in FIG. 2, performing a 101 point adjacent averaging smoothing operation, then subtracting the smoothed data from the raw data, and performing a 7 point adjacent averaging smoothing operation on the result. The upper trace (unpressed condition) has been shifted upward by 20,000 counts to avoid overlapping of the displayed traces. FIG. 5 shows the difference between the two traces shown in FIG. 4. This subtraction reveals Raman features attributable to blood. The area between the curve and zero in the region between 495 and 560 wavenumbers (arrow) was integrated to obtain a measure corresponding to blood glucose content. The ratio of this value to the area under the curve (yielding normalized integrated units) shown in FIG. 4 is proportional to blood glucose concentration.

Figure 6:
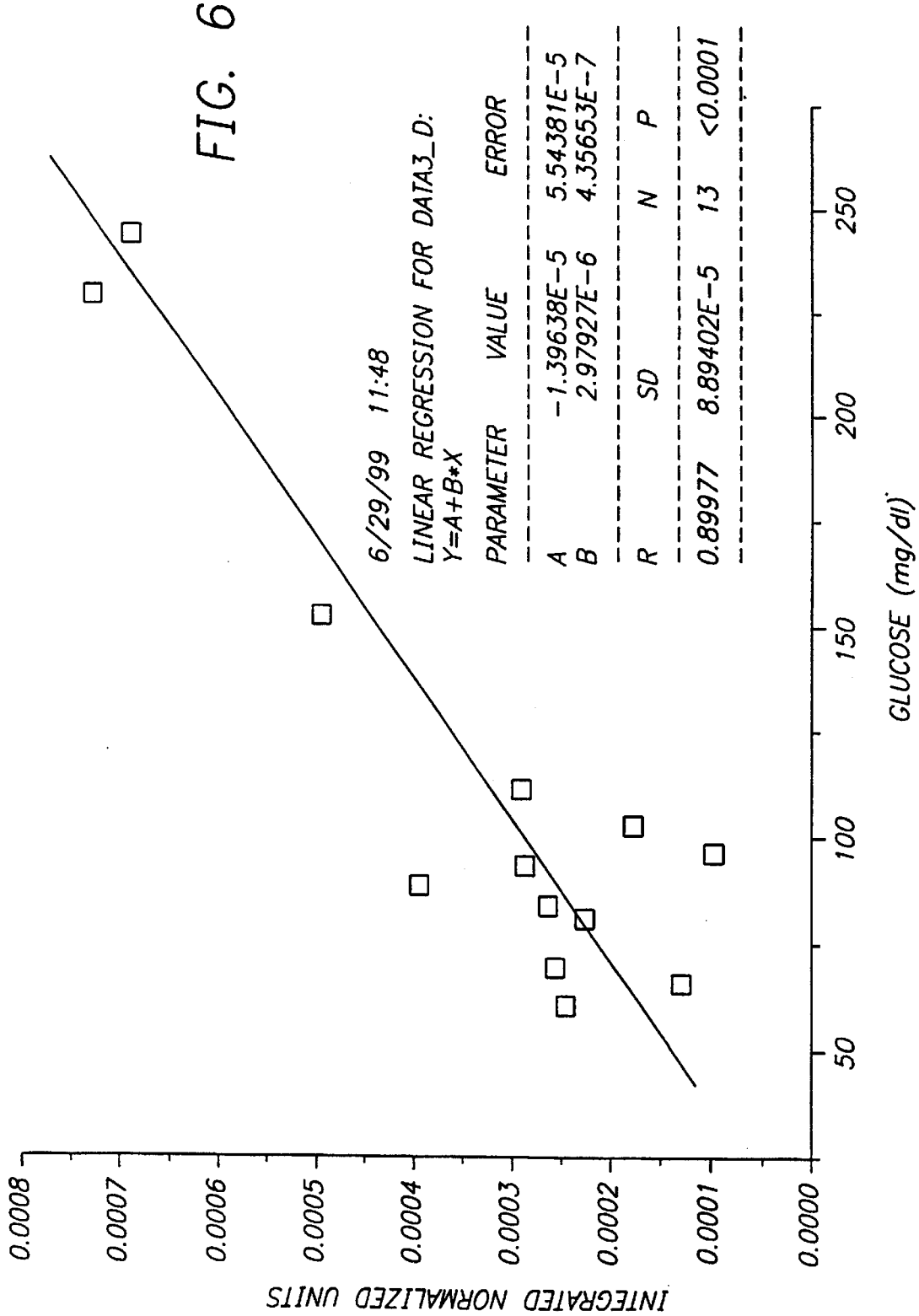
FIG. 6 shows the linear fit of integrated normalized units (Raman signal divided by blood volume) obtained by the methods employed as in FIGS. 1–4 for two diabetic and one normal subject plotted against actual blood glucose concentration (in mg/dl) measured from blood drawn from the same subjects and assayed by conventional techniques. Displayed are results of the linear regression analysis indicating a correlation of 0.89977, having a p value of less than 0.0001.

FIG. 6 shows the linear fit of integrated normalized units (Raman signal divided by blood volume) obtained for two diabetic and one normal subject plotted against actual blood glucose concentration (in mg/dl) measured from blood drawn from the same subjects and assayed by a physician using a HemaCue™ kit (HemaCue, Inc., Mission Viejo, Calif.) following manufacturer's instructions. Displayed are results of the linear regression analysis indicating a correlation of 0.89977, having a p value of less than 0.0001.

Example 5:
Absorption-Based Blood Volume Measurements from a Human Subject

This Example demonstrates that blood volume information can be derived from measuring absorption of light by the blood. The Example includes demonstrations that the signal is altered by known alterations in blood volume due to heartrate.

Materials & Methods

Figure 7:
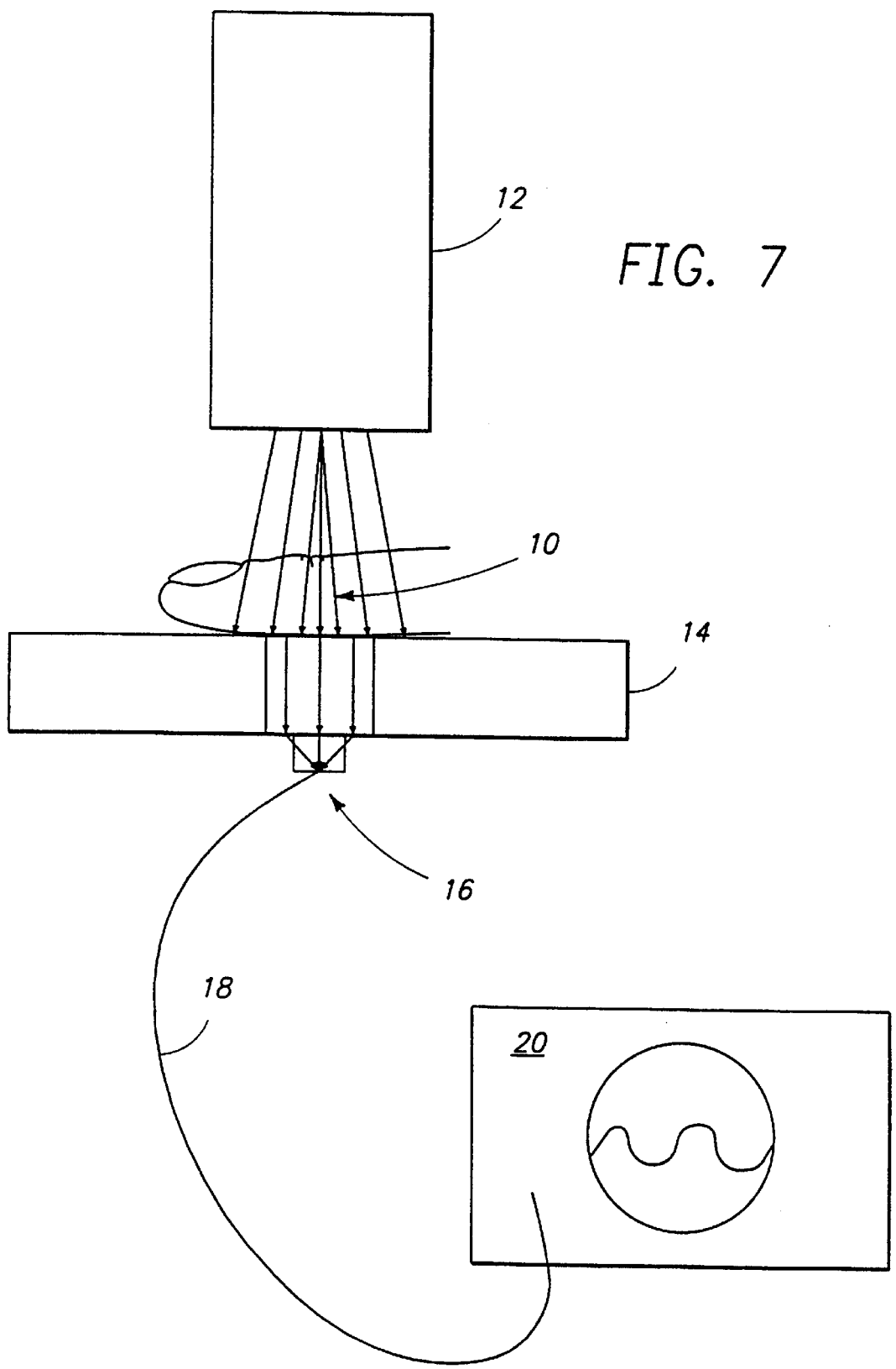
FIG. 7 is a schematic illustration of an apparatus used to collect the data shown in FIGS. 9–13. The finger 10 of a subject is placed under a light source 12, such as a flashlight, free-space coupled diode laser or fiber-coupled diode laser, and against a metal plate 14 having a hole or transparent region, at the other end of which is a lensed pickup diode 16 connected by wires 18 to an oscilloscope 20.
Figure 8:
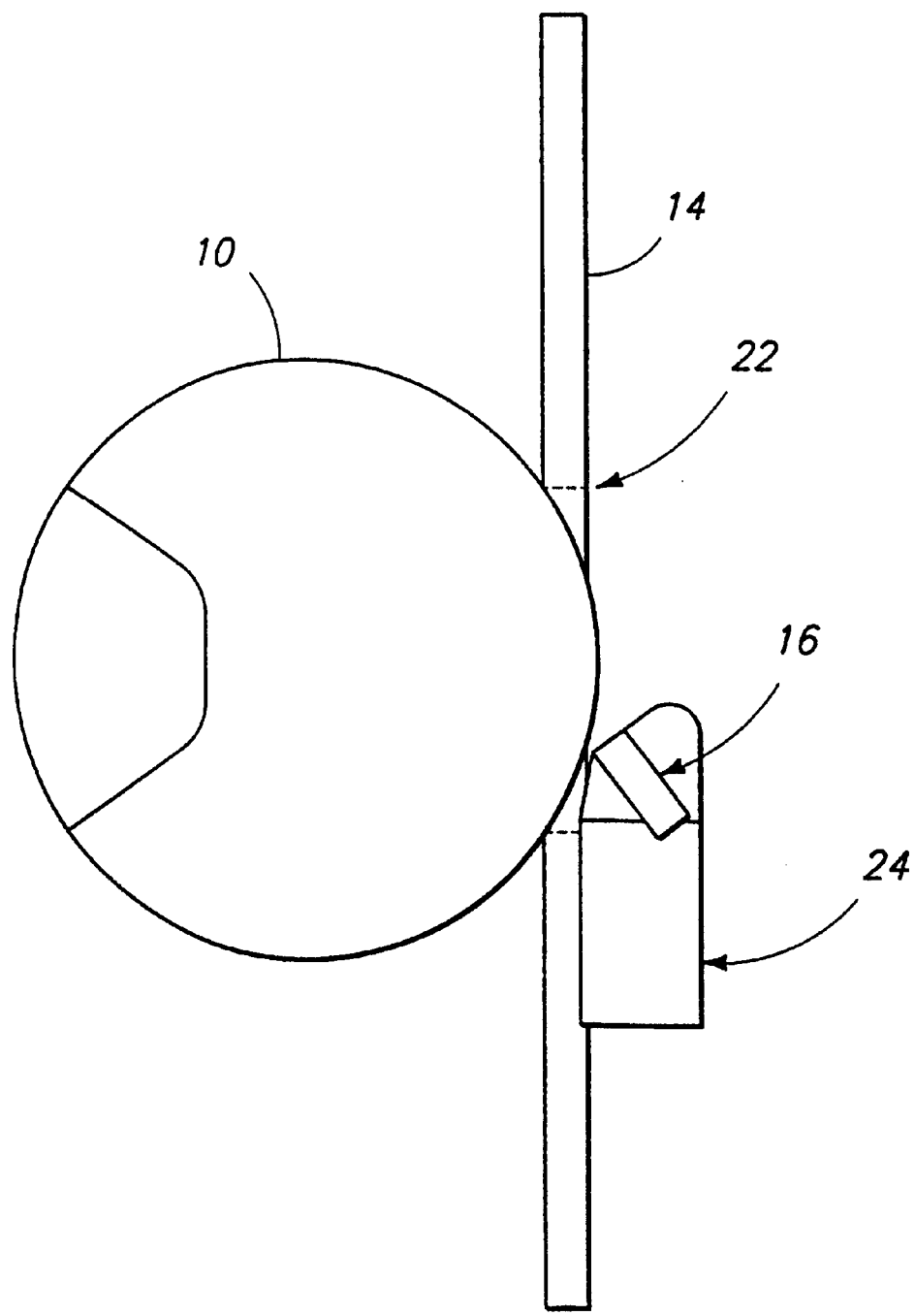
FIG. 8 is a cross-sectional view through the finger 10 shown in FIG. 7, and showing the finger 10 up against the hole 22 in the metal plate 14 and the angle of the lensed pickup diode 16 positioned on a diode mount 24.

A schematic illustration of the apparatus used to collect the data is shown in FIG. 7. The finger 10 of a subject was placed under a light source 12, e.g., a flashlight, free-space coupled 805 nm diode laser or fiber-coupled 805 nm diode laser (all three were used in different experiments), and against a metal plate 14 having a hole, at the other end of which is a lensed pickup diode (GaAs) 16 connected by wires 18 to an oscilloscope 20. FIG. 8 is a cross-sectional view through the finger 10 shown in FIG. 7, and shows the finger 10 up against the hole 22 in the metal plate 14 and the angle of the lensed pickup diode 16 positioned on a diode mount 24.

Results

Figure 9:
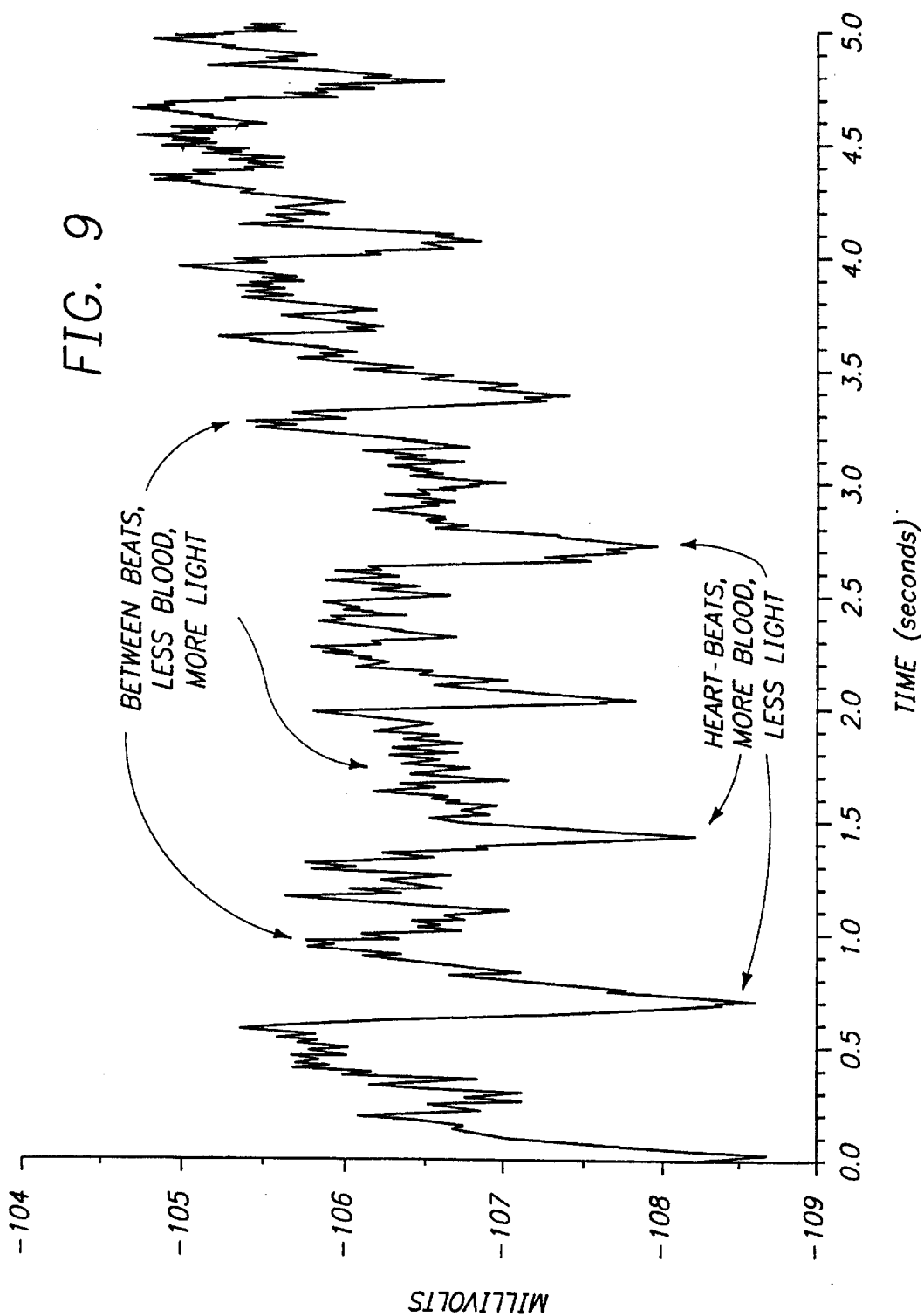
FIG. 9 shows light passing through a subject's finger placed on the apparatus shown in FIGS. 7 and 8 as measured using the lensed pickup diode 16 and plotted as millivolts over time, in seconds. As indicated in the Figure, between heartbeats, when less blood is present in the fingertip, more light passes through. Likewise, less light passes during beats and when more blood present and absorbing light.
Figure 10:
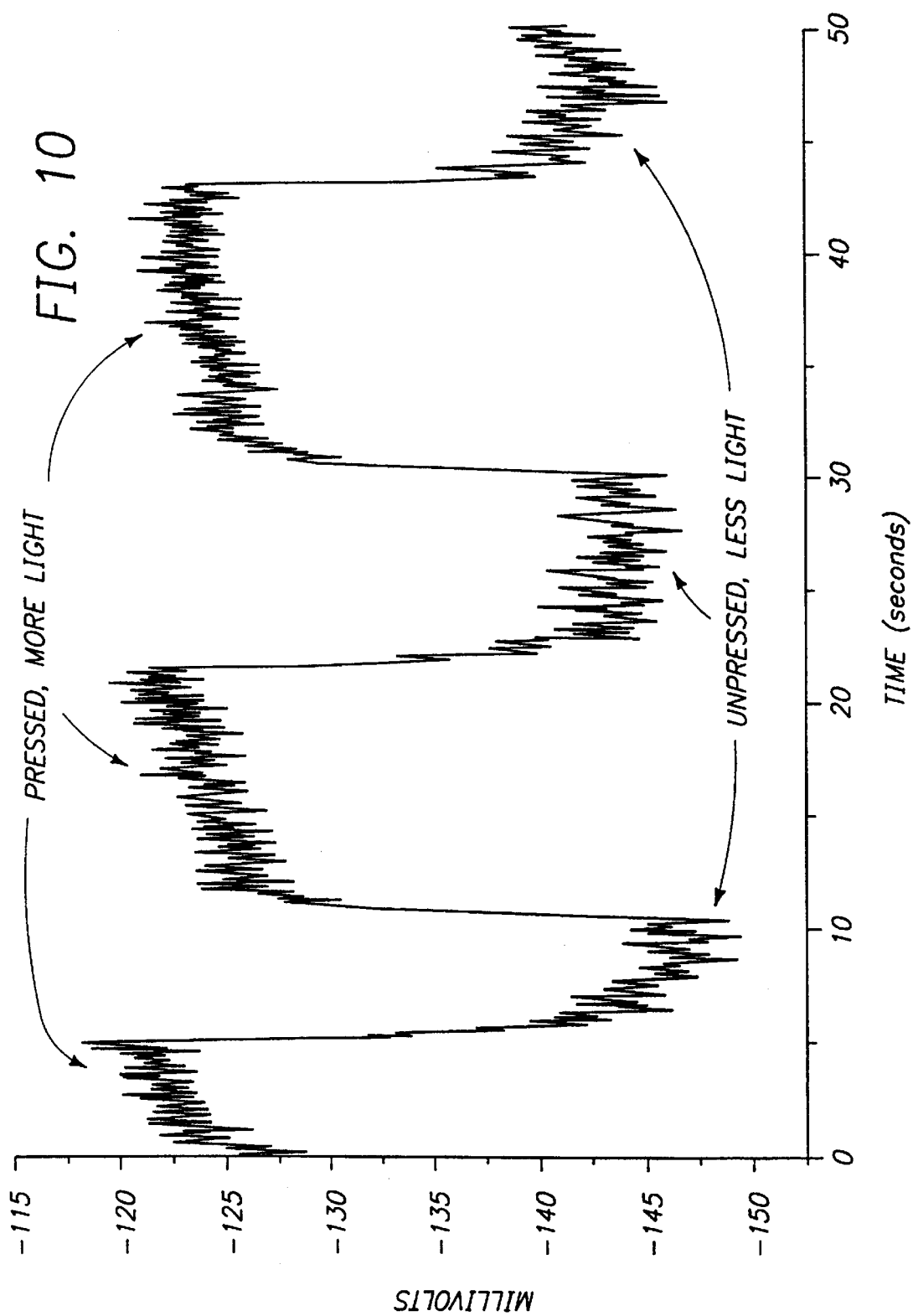
FIG. 10 shows data similar to that shown in FIG. 9, except that the subject has alternated between pressing the finger against the plate and unpressing the finger. When the finger is pressed against the metal plate, blood leaves the fingertip and more light passes through. Similarly, less light passes when the finger is unpressed and filled with blood. The difference between the traces in the pressed and unpressed states provides an alternate method of determining blood volume.

FIG. 9 shows light passing through a subject's finger placed on the apparatus measured using the lensed pickup diode 16 and plotted as millivolts over time, in seconds. As indicated in the Figure, between heartbeats, when less blood is present in the fingertip, more light passes through. Likewise, less light passes during beats and when more blood is present and absorbing light. FIG. 10 shows data similar to that shown in FIG. 9, except that the subject has alternated between pressing the finger against the plate and unpressing the finger. When the finger is pressed against the metal plate, blood leaves the fingertip and more light passes through. Similarly, less light passes when the finger is unpressed and filled with blood. The difference between the traces in the pressed and unpressed states provides an alternate method of determining blood volume.

Figure 11:
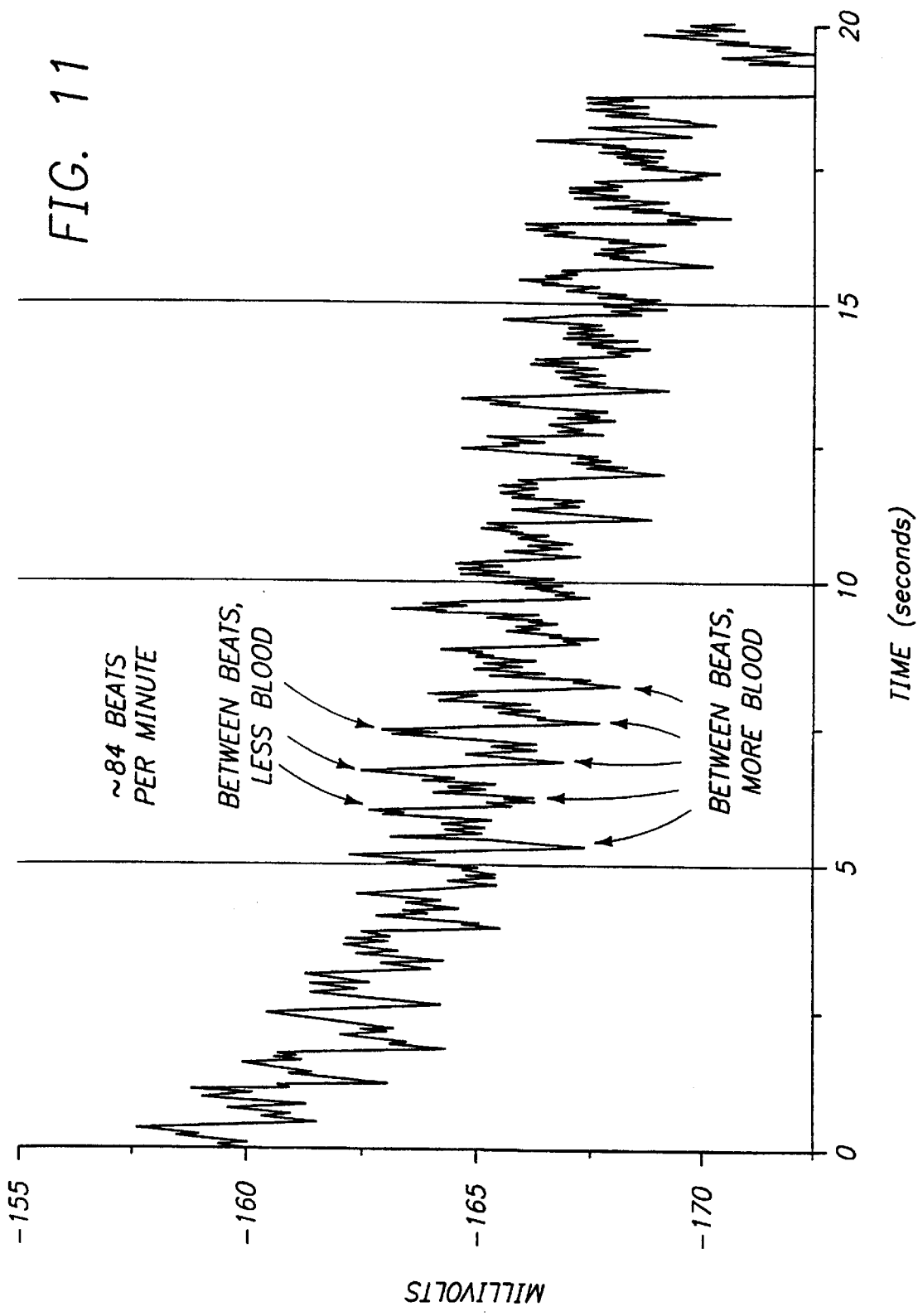
FIG. 11 shows data similar to that shown in FIG. 9, except that the subject had run in place for a few seconds prior to data collection. This activity increased heart rate and the effect of increased heart rate on fluctuations in light passing through the finger confirms that the source of the signal detected in FIGS. 8 and 9 is indeed changes in blood volume as a function of heartbeats.

FIG. 11 shows data similar to that shown in FIG. 9, except that the subject had run in place for a few seconds prior to data collection. This activity increased heart rate and the effect of increased heart rate on fluctuations in light passing through the finger confirms that the source of the signal detected in FIGS. 8 and 9 is indeed changes in blood volume as a function of heartbeats.

Figure 12:
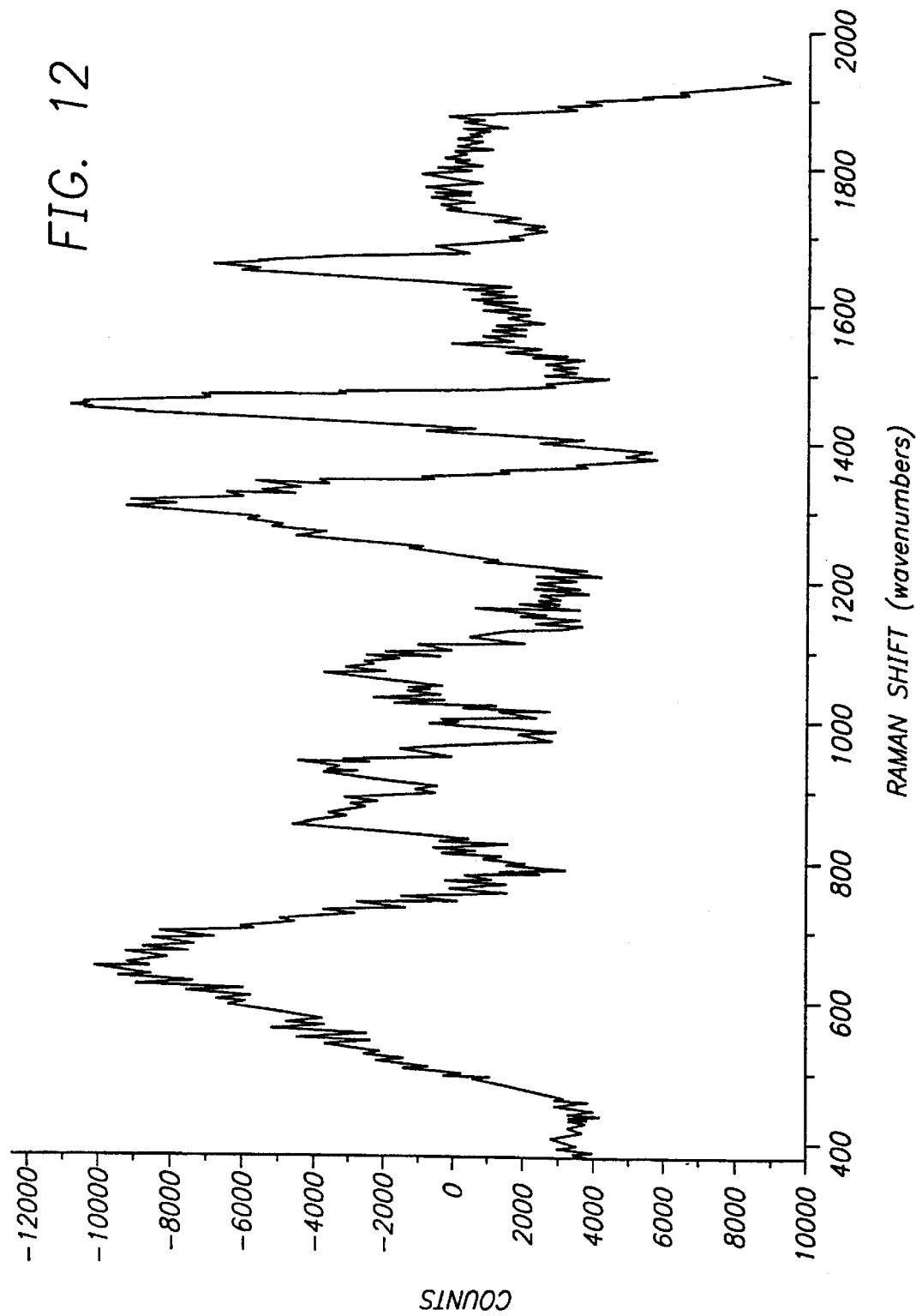
FIG. 12 shows spectral counts at wavenumbers ranging from about 380 to about 2000 collected from a fingertip in which blood volume was modulated with a tourniquet. Displayed are counts detected with the tourniquet in place subtracted from counts detected without the tourniquet. Note the negative-going peaks.

FIG. 12 shows spectral counts at wavenumbers ranging from about 380 to about 2000 collected from a fingertip in which blood volume was modulated with a tourniquet. Displayed are counts detected with the tourniquet in place subtracted from counts detected without the tourniquet. Note the negative-going peaks.

Figure 13:
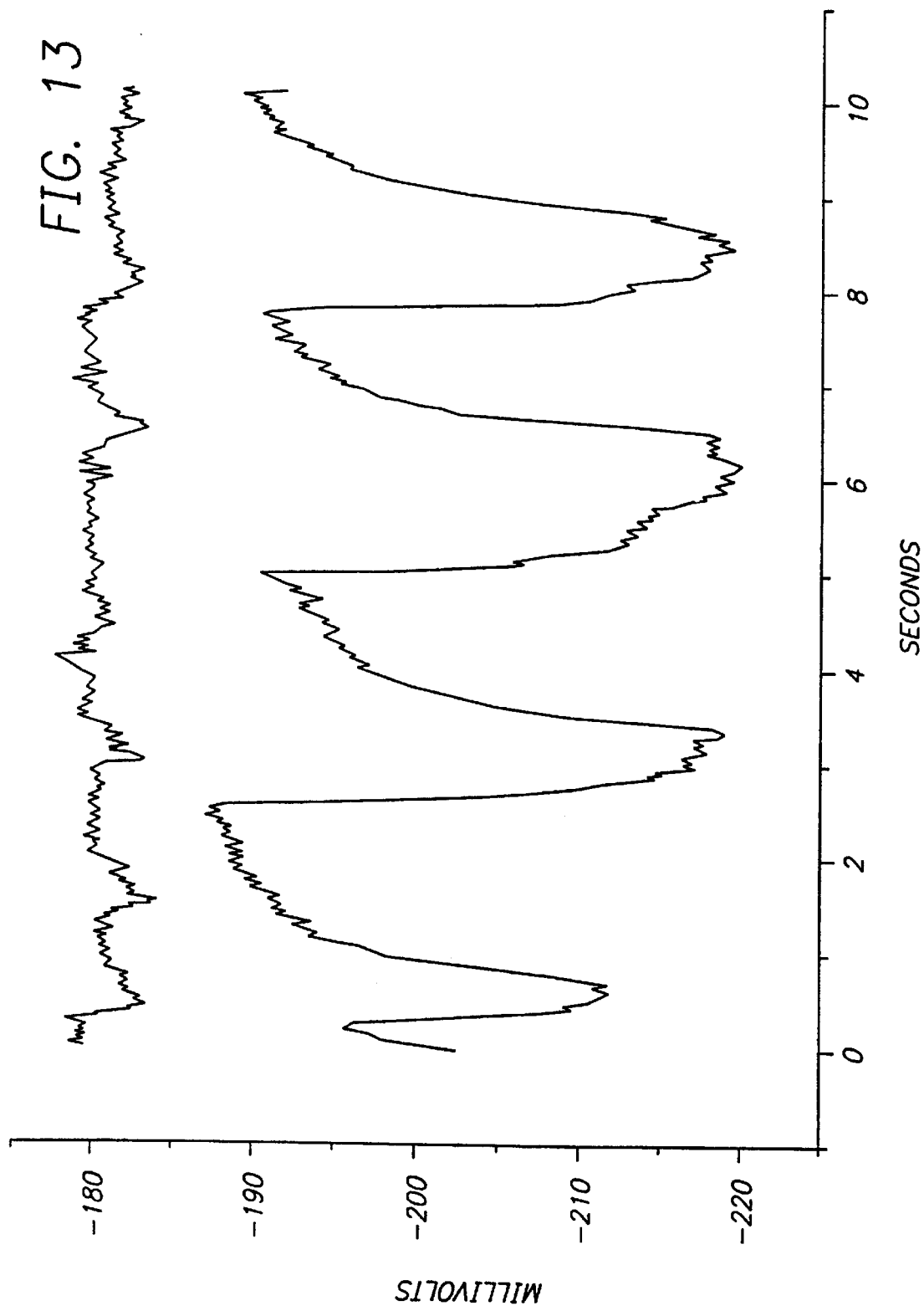
FIG. 13 shows light passing through the subject's finger as measured using the lensed pickup diode and plotted as millivolts over time, in seconds. The upper trace shows measurements taken with the tourniquet in place, and the lower trace shows measurements taken without the tourniquet.

FIG. 13 shows light passing through the subject's finger as measured using the lensed pickup diode and plotted as millivolts over time, in seconds. The upper trace shows measurements taken with the tourniquet in place, and the lower trace shows measurements taken without the tourniquet.

Those skilled in the art will appreciate other variations and modifications that can be adapted for the methods and apparatus disclosed herein without departing from the spirit and scope of the invention.

What is claimed is:

1. A noninvasive method of determining concentration of an analyte in blood of a subject comprising:
   a) irradiating a region of tissue of the subject with a light source;
   b) collecting fluorescence spectra emitted by the region of tissue, the quantity of fluorescence spectra being indicative of blood volume;
   c) collecting Raman spectra emitted by the region of tissue at a wavelength range that corresponds to the analyte, the quantity of Raman spectra being indicative of the amount of analyte; and
   d) dividing the collected Raman spectra by the collected fluorescence spectra to obtain a number proportional to the concentration of analyte per unit blood volume.

2. The method of claim 1, wherein the fluorescence and Raman spectra are collected while the region of tissue is in a blood-replete state and collected while the region of tissue is in a blood-depleted state, and wherein the method further comprises determining the integral of net collected spectra, net collected spectra being a difference between spectra collected while the region of tissue is in a blood-replete state and spectra collected while the region of tissue is in a blood-depleted state, wherein the dividing of step (d) is performed by dividing the integral of the net collected Raman spectra at the wavelength range corresponding to the analyte by the integral of the net collected fluorescence spectra.

3. The method of claim 2, wherein the net collected Raman spectra is determined by:

$$I(\lambda)^{unp} - I(\lambda)^{pre} = \{\{(^eI_s) + (^fI_s) + (^rI_s)\} + \{(^eI_{bu}) + (^fI_{bu}) + (^rI_{bu})\}\} e^{-[b_{unp}]d} - \{\{(^eI_s) + (^fI_s) + (^rI_s)\} + \{(^eI_{bp}) + (^fI_{bp}) + (^rI_{bp})\}\} e^{-[b_{pre}]d}$$

where:
   $I(\lambda)$ = collected light intensity at wavelength $\lambda$.
   unp or u refers to an unpressed or blood-replete state
   pre or p refers to a pressed or blood-depleted state
   $(^eI_s)$ = intensity of light scattered by elastic processes from skin
   $(^fI_s)$ = intensity of fluorescence from skin
   $(^rI_s)$ = intensity of Raman scattering from skin
   $(^eI_b)$ = intensity of light scattered by elastic processes from blood
   $(^fI_b)$ = intensity of fluorescence from blood
   $(^rI_b)$ = intensity of Raman scattering from blood
   [b] = concentration of hemoglobin
   d = depth beneath air-stratum corneum interface from where $I(\lambda)$ originates.

4. The method of claim 2, further comprising enhancing the spectra collected by:
   i) performing a 61–501 point adjacent averaging smoothing operation on the net collected spectra;
   ii) subtracting the smoothed spectra from the net collected spectra; and
   iii) performing a 3–27 point adjacent averaging smoothing operation on the result of step (ii).

5. The method of claim 4, wherein the adjacent averaging smoothing operation of step (i) is a 85–201 point smoothing operation.

6. The method of claim 5, wherein the adjacent averaging smoothing operation of step (i) is a 101 point smoothing operation.

7. The method of claim 4, wherein the adjacent averaging smoothing operation of step (iii) is a 7 point smoothing operation.

8. The method of claim 2, wherein the blood-depleted state is achieved by applying a tourniquet to the tissue or by pressing the tissue against a surface.

9. The method of claim 2, wherein the blood-replete and blood-depleted states are achieved by applying an ultrasonic transducer to the region of tissue.

10. The method of claim 1, wherein the light source emits light having a wavelength of about 785 nm to about 850 nm.

11. The method of claim 10, wherein the wavelength is about 785 nm.

12. The method of claim 10, wherein the wavelength is about 805 or about 808 nm.

13. The method of claim 1, wherein the light source is a laser.

14. The method of claim 1, wherein the analyte is glucose, urea, creatinine, total protein, free fatty acids, monoglycerides, diglycerides, triglycerides, creatinine, alpha helix exposed exchangeable protein associated amide protons, cholesterol, pyruvate, tyrosine, tryptophan, bicarbonate, electrolytes, lactic acid, a drug, $O_2$, $CO_2$ or NO.

15. The method of claim 1, wherein the region of tissue is a fingertip.

16. A noninvasive method of determining concentration of an analyte in blood of a subject comprising:

a) irradiating a region of tissue of the subject with a light source;

b) collecting Raman spectra emitted by the region of tissue at a wavelength range that corresponds to the analyte, the quantity of Raman spectra being indicative of the amount of analyte; and c) measuring absorption of incident light by the region of tissue, the amount of absorbed light being indicative of blood volume;

d) dividing the collected Raman spectra by the amount of absorbed incident light to obtain the concentration of analyte per unit blood volume.

17. The method of claim 16, wherein the collecting of step (b) and the measuring of step (c) are performed while the region of tissue is in a blood-replete state and while the region no of tissue is in a blood-depleted state, and wherein the dividing of step (d) is performed by dividing the net collected Raman spectra by the net absorbed light, wherein net refers to the difference between the blood-replete and blood-depleted states.

18. The method of claim 17, further comprising enhancing the spectra collected by:

i) performing a 61–501 point adjacent averaging smoothing operation on the net collected spectra;

ii) subtracting the smoothed spectra from the net collected spectra; and iii) performing a 3–27 point adjacent averaging smoothing operation on the result of step (ii).

19. The method of claim 18, wherein the adjacent averaging smoothing operation of step (i) is a 85–201 point smoothing operation.

20. The method of claim 19, wherein the adjacent averaging smoothing operation of step (i) is a 101 point smoothing operation.

21. The method of claim 18, wherein the adjacent averaging smoothing operation of step (iii) is a 7 point smoothing operation.

22. The method of claim 17, wherein the blood-depleted state is achieved by applying a tourniquet to the tissue or by pressing the tissue against a surface.

23. The method of claim 17, wherein the blood-replete and blood-depleted states are achieved by applying an ultrasonic transducer to the region of tissue.

24. The method of claim 16, wherein the light source emits light having a wavelength of about 785 nm to about 850 nm.

25. The method of claim 24, wherein the wavelength is about 785 nm.

26. The method of claim 24, wherein the wavelength is about 805 or about 808 nm.

27. The method of claim 16, wherein the light source is a laser.

28. The method of claim 16, further comprising irradiating the tissue with a second light source having a wavelength that corresponds to an isosbestic point for oxy-deoxyhemoglobin.

29. The method of claim 28, wherein the second light source is a laser, a black body source or a light emitting diode.

30. The method of claim 30, wherein the light source of step (a) has a wavelength of about 785 nm and the second light source has a wavelength of about 805 or about 808 nm.

31. The method of claim 16, wherein the analyte is glucose, urea, creatinine, total protein, free fatty acids, monoglycerides, diglycerides, triglycerides, creatinine, alpha helix exposed exchangeable protein associated amide protons, cholesterol, pyruvate, tyrosine, tryptophan, bicarbonate, electrolytes, lactic acid, a drug, $O_2$, $CO_2$ or NO.

32. The method of claim 16, wherein the region of tissue is a fingertip.

* * * * *

UNITED STATES PATENT AND TRADEMARK OFFICE
CERTIFICATE OF CORRECTION

PATENT NO.    : 6,289,230 B1
DATED         : September 11, 2001
INVENTOR(S)   : Joseph Chaiken and Charles M. Peterson It is certified that error appears in the above-identified patent and that said Letters Patent is hereby corrected as shown below:

Column 26,
Line 40, after "claim", "30" should read -- 28 --.

Signed and Sealed this

Twenty-sixth Day of November, 2002

Attest:

Attesting Officer

JAMES E. ROGAN
*Director of the United States Patent and Trademark Office*